United States Patent
Liu et al.

(10) Patent No.: US 11,125,713 B2
(45) Date of Patent: Sep. 21, 2021

(54) ELECTROCHEMICAL SENSOR FOR ANALTYE DETECTION

(71) Applicant: CASE WESTERN RESERVE UNIVERSITY, Cleveland, OH (US)

(72) Inventors: Chung Chiun Liu, Cleveland Heights, OH (US); Yifan Dai, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 171 days.

(21) Appl. No.: 16/355,314

(22) Filed: Mar. 15, 2019

(65) Prior Publication Data

US 2020/0018717 A1    Jan. 16, 2020

Related U.S. Application Data

(63) Continuation-in-part of application No. 15/314,380, filed as application No. PCT/US2015/032399 on May 26, 2015, now Pat. No. 10,883,956.

(60) Provisional application No. 62/644,119, filed on Mar. 16, 2018, provisional application No. 62/657,326, filed on Apr. 13, 2018, provisional application No. 62/084,188, filed on Nov. 25, 2014, provisional application No. 62/003,205, filed on May 27, 2014.

(51) Int. Cl.
  *G01N 27/327*    (2006.01)
  *G01N 33/543*    (2006.01)

(52) U.S. Cl.
  CPC ..... *G01N 27/3276* (2013.01); *G01N 33/5438* (2013.01)

(58) Field of Classification Search
  None
  See application file for complete search history.

(56) References Cited

U.S. PATENT DOCUMENTS

| | | |
|---|---|---|
| 4,571,292 A | 2/1986 | Liu et al. |
| 4,655,880 A | 4/1987 | Liu |
| 6,623,620 B2 | 9/2003 | Lai et al. |
| 2004/0194302 A1* | 10/2004 | Bhullar ............ G01N 33/5438 29/847 |
| 2008/0027135 A1 | 1/2008 | Sondek et al. |
| 2012/0046181 A1 | 2/2012 | Harb et al. |
| 2017/0102350 A1 | 4/2017 | Lu |
| 2017/0184564 A1 | 6/2017 | Liu et al. |
| 2017/0248541 A1 | 8/2017 | Liu |
| 2019/0204268 A1 | 7/2019 | Liu et al. |

OTHER PUBLICATIONS

E.A. Smith, et al. "Formation, Spectroscopic Characterization, and Application of Sulfhydryl-Terminated Alkanethiol Monolayers for the Chemical Attachment of DNA onto Gold Surfaces", Langmuir, 17(8): p. 2502-2507, Apr. 2001.*

(Continued)

*Primary Examiner* — J. Christopher Ball
(74) *Attorney, Agent, or Firm* — Tarolli, Sundheim, Covell & Tummino LLP

(57) ABSTRACT

A sensor for the detection of analyte includes a substrate, a working electrode and counter electrode formed on a surface of the substrate, and an antibody bioconjugated to a surface of an exposed portion of the working electrode.

19 Claims, 17 Drawing Sheets

(56) References Cited

OTHER PUBLICATIONS

Q. Xue, et al. "An integrated micro immunosensor for hemoglobin-A1c level detection", iI Pr5oceedings of 2010 IEEE/ASME International Conference on Mechatronic and Embedded Systems and Applications, p. 208-212, Jul. 2010.

First Named Inventor: Chung Chiun Liu; Title: System and Methods for the Detection of Biomarkers of Neurodegenerative Disorders; U.S. Appl. No. 15/970,738, filed May 3, 2018; Final Office Action; Notification dated Sep. 22, 2020.

First Named Inventor: Chung Chiun Liu; Title: System and Methods for the Detection of HBA1C; U.S. Appl. No. 15/973,218, filed May 7, 2018; Final Office Action; Notification dated Sep. 1, 2020.

First Named Inventor: Chung Chiun Liu; Title: System and Method for Detecting LYSYL Oxidase-Like 2 Protein (LOXL2) and Breast Cancer; U.S. Appl. No. 16/168,630, filed Oct. 23, 2018; Office Action; Notification dated Sep. 21, 2010; 7 pgs.

First Named Inventor: Chung Chiun Liu; Title: System and Methods for the Detection of Biomarkers of Glypican-1; U.S. Appl. No. 16/118,216, filed Aug. 30, 2018; Final Office Action; Notification dated Oct. 8, 2020.

Karalemas et al., Talanta, 2000, 53:391-402.

Moreno-Bueno, et al., EMBO Mol Med., 2011, 3:528-544.

* cited by examiner

ELECTROCHEMICAL SENSOR FOR ANALTYE DETECTION

RELATED APPLICATION

This application claims priority from U.S. Provisional Application No. 62/644,119, filed Mar. 16, 2018 and 62/657,326 filed Apr. 13, 2018, this application is also a Continuation-In-Part of U.S. Ser. No. 15/314,380, filed Nov. 28, 2016, which is a National Phase filing of PCT/US2015/032399, filed May 26, 2015, which claims priority to U.S. Provisional No. 62/084,188, filed Nov. 25, 2014 and 62/003,205, filed May 27, 2014, the subject matter of which are incorporated herein by reference in their entirety.

BACKGROUND

A typical disposable electrochemical sensor includes a substrate film upon which a layer of conductive material is deposited and patterned to form electrodes. Traditionally, electrochemical cells, or biosensors, are comprised of three electrodes, a working electrode or sensing electrode, a reference electrode, and a counter electrode or auxiliary electrode. The working electrode is where the reaction of interest occurs at a fixed applied potential versus the reference electrode. The reference electrode functions to maintain a stable electrical potential on the working electrode. The counter electrode allows current to flow between the working electrode and the counter electrode so as not to disturb the reference electrode function. In cases when the system potential is inherently stable or small fluctuations in potential are not a concern, the reference and counter electrodes can be combined into a single reference/counter electrode paired with a working electrode. In some instances electrochemical biosensors use amperometry to quantify specific analyte concentration(s). The working electrode provides a response proportional to its exposed surface area. During fabrication, the manufacture closely controls the process variation associated with the working electrode area.

Normally the working electrode is formed from two or more elements. One element is a conductive layer that forms the active element facilitating electron transfer to or from an electro-active species which are generated when the sample is applied to the sensor. A second element is a dielectric layer that defines, along with the first element, the actual dimensions of the working electrode that is in contact with the sample fluid. The second element forms a window over a portion of the conductive layer. Variation in either element may result in a variation in the sensor response. The second element or dielectric layer may therefore directly influence the accuracy of the reading.

SUMMARY

Embodiments described herein relate to electrochemical biosensors that are capable of providing analysis of analytes in a sample of interest. The biosensors can produce a signal that is related to the presence or quantity of the analyte being detected in a sample, such as a biological sample. In some embodiments, the biosensor can be used quantify a biological marker, such as TDP-43, AMACR, or PSA, that is present in a biological sample, such as a bodily fluid (e.g., serum, blood, plasma, saliva, urine, mucous, breath, etc.).

In some embodiments, the biosensor includes a substrate, a working electrode formed on a surface of the substrate, a counter electrode formed on the surface of the substrate, and a dielectric layer covering a portion of the working electrode and counter electrode and defining an aperture exposing other portions of the working electrode and counter electrode. An antibody that is selective to the analyte of interest is conjugated to a surface of the exposed portion of the working electrode with a linker. The linker is about 3 to about 10 atoms in length and includes a first end and a second end. The first end include an acyl group that is bound to a lysine group of the antibody. The second end includes a sulfhydryl group that is bound to the surface of the working electrode. The surface of the working electrode is free of a self-assembled monolayer.

In some embodiments, the antibody can include at least one of an anti-TDP-43, anti-AMACR antibody, or anti-PSA antibody, and the analyte can be TDP-43, AMACR, or PSA, respectively.

The biosensor can also include a measuring device for applying a voltage potential to the working electrode, counter electrode, and/or reference electrode and measuring the current flow between the working electrode and counter electrode. The interaction of the antibody and the bound analyte, e.g., the bound TDP-43, can be detected using electrochemical analytical techniques, such as cyclic voltammetry (CV), differential pulse voltammetry (DPV), to determine the presence of the analyte (e.g., TDP-43) in the biological sample.

Other embodiments described herein relate to a method of forming an electrochemical sensor for detection of an analyte of interest. The method includes providing an antibody that is selective to the analyte of interest. A heterobifunctional linker is conjugated to the antibody. The linker includes an acyl group and a sulfhydryl group. A sensor is provided that includes a substrate, a working electrode formed on a surface of the substrate, a counter electrode formed on the surface of the substrate, and an optional reference electrode formed on the surface of the substrate. A dielectric layer covers a portion of the working electrode and counter electrode and defines an aperture exposing portions of surfaces of the working electrode and counter electrode. The antibody conjugated to the linker is reacted with the surface of the exposed portion of the working electrode to link the antibody to the working electrode.

In some embodiments, the linker is conjugated to a lysine residue of the antibody. The linker also includes a sulfhydryl group that reacts with the surface of the working electrode. For example, the linker can include an N-hydroxysuccinimide ester that reacts with an amine group of a lysine residue and a sulfhydryl group that reacts with the surface of the working electrode. The sulfhydryl group can also be coupled to a protecting group that is removed prior to reaction of the sulfhydryl group with the surface of the exposed portion of the working electrode. In some embodiments, the linker include at least one of N-succinimidyl S-acetylthioacetate or N-succinimidyl S-acetylthiopropionate.

In some embodiments, the working electrode and the counter electrode include metalized films, such as gold, platinum, palladium, silver, alloys thereof, and composites thereof. The metalized films can be provided on the surface of the substrate by sputtering or coating the films on the surface. The working electrode and the counter electrode can be formed using laser ablation to define the dimensions of the working electrode and the counter electrode. The surface of the working electrode can be free of a self-assembled monolayer.

In some embodiments, the antibody can include at least one of an anti-TDP-43, anti-AMACR, or anti-PSA antibody and be used to detect TDP-43, AMACR, or PSA respectively in a biological sample.

In other embodiments, the antibody can be functionalized to the surface of the working electrode by providing the antibody in a solution that is continuously flowed over the surface of the electrode.

DETAILED DESCRIPTION

Figure 1:
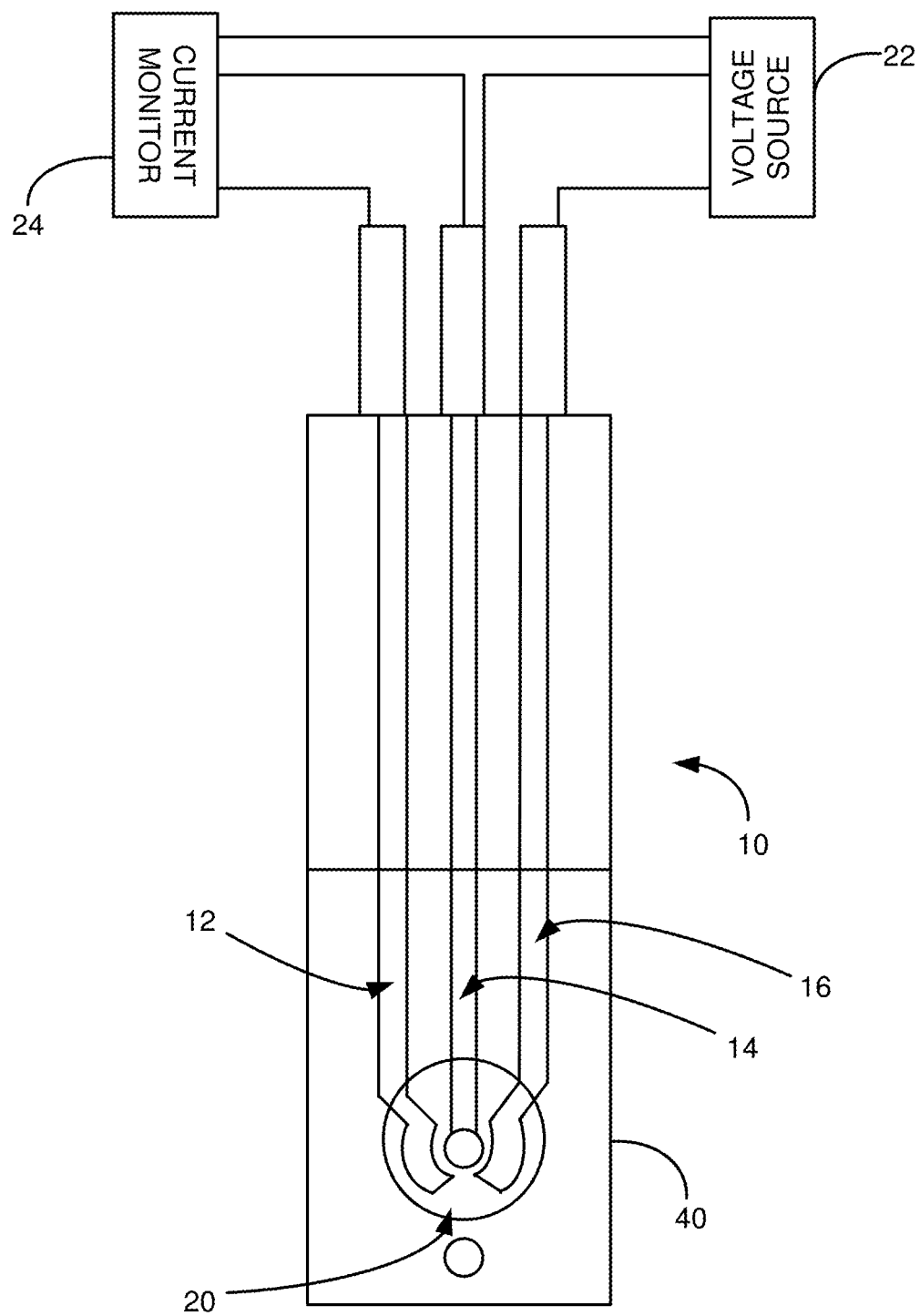
FIG. 1 is a schematic illustration of a biosensor in accordance with an aspect of the application.

Unless specifically addressed herein, all terms used have the same meaning as would be understood by those of skilled in the art of the subject matter of the application. The following definitions will provide clarity with respect to the terms used in the specification and claims.

As used herein, the term "monitoring" refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As used herein, the term "quantitative data" or "quantitative level" or "quantitative amount" refers to data, levels, or amounts associated with any dataset components (e.g., markers, clinical indicia,) that can be assigned a numerical value.

As used herein, the term "subject" refers to a human or another mammal. Typically, the terms "subject" and "patient" are used herein interchangeably in reference to a human individual.

As used herein, the term "bodily sample" refers to a sample that may be obtained from a subject (e.g., a human) or from components (e.g., tissues) of a subject. The sample may be of any biological tissue or fluid with, which analytes described herein may be assayed. Frequently, the sample will be a "clinical sample", i.e., a sample derived from a patient. Such samples include, but are not limited to, bodily fluids, e.g., saliva, breath, urine, blood, plasma, or sera; and archival samples with known diagnosis, treatment and/or outcome history. The term biological sample also encompasses any material derived by processing the bodily sample. Processing of the bodily sample may involve one or more of, filtration, distillation, extraction, concentration, inactivation of interfering components, addition of reagents, and the like.

As used herein, the terms "normal" and "healthy" are used interchangeably. They refer to an individual or group of individuals who have not shown any symptoms of a disease, condition, or pathology to be detected, and have not been diagnosed with the disease, condition, or pathology. Preferably, the normal individual (or group of individuals) is not on medication. In certain embodiments, normal individuals have similar sex, age, body mass index as compared with the individual from, which the sample to be tested was obtained. The term "normal" is also used herein to qualify a sample isolated from a healthy individual.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal.

Embodiments described herein relate to electrochemical biosensors that are capable of providing analysis of various analytes or biomolecules using biological recognition elements. The biosensor can produce a signal that is related to the presence or quantity of the analytes being detected in a sample, such as a biological sample. In some embodiments, the biosensor can be used to detect proteins, polypeptides, cytokines, micorganisms, polynucleotides (mRNA, DNA, cDNA, mRNA, etc.) that are present in a biological sample, such as a bodily fluid (e.g., serum, blood, plasma, saliva, urine, mucous, breath, etc.). In some embodiments, the biosensor can be used quantify biological marker, such as TDP-43, AMACR, or PSA, that is present in a biological sample, such as a bodily fluid (e.g., serum, blood, plasma, saliva, urine, mucous, breath, etc.). The biosensors described herein can provide a single use, disposable, and cost-effective means for simple point-of-care, real time assessment of analytes in biological samples, such as bodily fluids obtained by non-invasive or minimally invasive means.

FIG. 1 illustrates a biosensor 10 in accordance with an embodiment of the application. The sensor 10 is a three-electrode sensor including a counter electrode 12, a working electrode 14, and a reference electrode 16 that are formed on a surface of a substrate. A dielectric layer 40 covers a portion of the working electrode 12, counter electrode 14 and reference electrode 16. The dielectric layer 40 includes an aperture 20 that defines a detection region of the working electrode 12, counter electrode 14, and reference electrode 16, which is exposed to samples containing an analyte to be detected. An antibody (not shown) that is selective to the analyte of interest is conjugated or linked to a surface of the exposed portion of the working electrode with a linker. The surface of the working electrode can be free of a self-assembled monolayer. The antibody antibody can bind selectively to the analyte in the biological sample.

The biosensor can also include a voltage source 22 for applying a voltage potential to the working electrode, counter electrode, and/or reference electrode and a measuring device or current monitor 24 for measuring the current flow between the working electrode and counter electrode. The interaction of the antibody and the analyte can be detected using electrochemical analytical techniques, such as cyclic voltammetry (CV), differential pulse voltammetry (DPV), to determine the presence of the analyte in the sample.

The working electrode 14 is poised at an appropriate electrochemical potential such that the current that flows through the electrode changes when the antibody binds to the analyte in the sample. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, carbon, alloys thereof, and composites thereof.

The antibody, which is conjugated or linked to the working electrode, is an antibody that binds selectively to the analyte. In some embodiments, the antibody can include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982,299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984,312: 604-608; S. Takeda et al., Nature, 1985, 314: 452-454). Antibodies to be used in the biosensor can be purified by methods well known in the art (see, for example, S. A. Minden, "Monoclonal Antibody Purification", 1996, IBC Biomedical Library Series: Southbridge, Mass.). For example, anti-TDP-43 antibodies, anti-AMACR, and/or anti-PSA antibodies can be affinity purified by passage over a column to which a protein marker or fragment thereof is bound. The bound antibodies can then be eluted from the column using a buffer with a high salt concentration.

In some embodiments, the antibody specifically binds to a cancer biomarker. Examples of cancer biomarkers include AMACR or PSA (prostate cancer), Carbohydrate antigen 125 (CA125) (ovarian cancer), human epididymis protein 4 (HE4) (ovarian cancer), BRAC1/BRAC2 (breast cancer, ovarian cancer), AFP (liver cancer), BCR-ABL (chronic myeloid leukemia), BRAF V600E (melanoma/colorectal cancer), KIT (gastrointestinal stromal tumor), PSA (prostate cancer), S100 (melanoma), KRAS (lung), CIZL (lung), and EGFR (colorectal/lung).

In other embodiments, the antibody can be an anti-TDP-43 antibody that selectively binds to TDP-43 in a sample from a subject for the detection of Alzheimer's disease in the subject. In other embodiments, the antibody can be an anti-AMACR antibody that selectively binds to AMACR in a sample from a subject for the detection of prostate cancer in the subject. In still other embodiments, the antibody can be an anti-PSA antibody that selectively binds to PSA in a sample from a subject for the detection of prostate cancer in the subject. An anti-TDP-43 antibody, anti-AMACR antibody, or anti-PSA antibody that binds selectively to TDP-43, AMACR, or PSA, respectively, can be a monoclonal or polyclonal antibody that binds selectively or specifically to TDP-43, AMACR, or PSA, respectively. Anti-TDP-43 antibodies, anti-AMACR antibodies, or anti-PSA antibodies, having binding affinities in the picomolar to micromolar range are suitable. Such interaction can be reversible.

Instead of being prepared, anti-TDP-43 antibodies, anti-AMACR, and/or anti-PSA antibodies to be used in the methods described herein may be obtained from scientific or commercial sources.

The linker used to link or conjugate the antibody to the surface of the working electrode can be a heterobifunctional linker of about 3 to about 10 atoms in length and include a first end and a second end. The first end can include an acyl group that is bound to an amine group of an amino acid residue of the antibody. The amine group can include, for example, an amine group of a lysine residue of the antibody.

The second end can include a sulfhydryl group that is reactive with and bound to the bare surface of the working electrode. The first end and the second end of the linker can be separated with a branched, unbranched, or straight alkane chain of about 1 to about 8 carbons in length to allow minimal distance between the antibody and the surface of the working electrode.

For example, the linker can include an N-hydroxysuccinimide ester that reacts with an amine group of a lysine residue and a sulfhydryl group that reacts with the surface of the working electrode. The sulfhydryl group can also be coupled to a protecting group that is removed prior to reaction of the sulfhydryl group with the surface of the exposed portion of the working electrode. In some embodiments, the linker can include at least one of N-succinimidyl S-acetylthioacetate or N-succinimidyl S-acetylthiopropionate.

Advantageously, it was found that conjugation of the heterobifunctional linker to the antibody prior to conjugation of the linker to the working electrode can shorten the preparation process of the sensor, enhance the coverage of the surface of working electrode, minimize pinhole effects and enhance the sensitivity of the sensor for the analyte.

In order to minimize any non-specific binding on the working electrode surface and blocking any open surface area of the working electrode at least one blocking agent can be applied to the surface of the working electrode once the antibody has been conjugate or linked to the working electrode. The blocking agent can enhance the reproducibility and sensitivity of the biosensor by minimizing non-specific interactions on the working electrode. In some embodiments, the blocking agent can include dithiothreitol or casein. The blocking agent can be applied to the surface of the working at an amount effective to minimize non-specific binding of proteins or other molecules on the surface of the working electrode.

The voltage source 22 can apply a voltage potential to the working electrode 14 and reference and/or counter electrode 16, 12, depending on the design of the sensor 10. The current between the working electrode 14 and counter electrode 16 can be measured with the measuring device or meter 24. Such current is dependent on interaction of the analyte with the antibody on the working electrode.

The amount or level of current measured is proportional to the level or amount of analyte in the biological sample. In some embodiments, where the sample is a bodily sample obtained from a subject, once the current level generated by the reaction solution tested with the sensor is determined, the level can be compared to a predetermined value or control value to provide information for diagnosing or monitoring of the condition, pathology, or disorder in a subject that is associated with presence or absence of the analyte.

The current level generated by sample obtained from the subject can be compared to a current level of a sample previously obtained from the subject, such as prior to administration of a therapeutic. Accordingly, the methods described herein can be used to measure the efficacy of a therapeutic regimen for the treatment of a condition, pathology, or disorder associated with the level of the analyte in a subject by comparing the current level obtained before and after a therapeutic regimen. Additionally, the methods described herein can be used to measure the progression of a condition, pathology, or disorder associated with the presence or absence of the analyte in a subject by comparing the current level in a bodily sample obtained over a given time period, such as days, weeks, months, or years.

The current level generated by a sample obtained from a subject may also be compared to a predetermined value or control value to provide information for determining the severity or aggressiveness of a condition, pathology, or disorder associated with analyte levels in the subject. A predetermined value or control value can be based upon the current level in comparable samples obtained from a healthy or normal subject or the general population or from a select population of control subjects.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

The biosensor illustrated in FIG. 1 can be fabricated on a substrate formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices can thus be formed on a common substrate. As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a gold film with a thickness of about 300A to about 2000A can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing techniques.

A heterobifunctional linker can be conjugated to the antibody. By way of example, a heterobifunctional linker, such as N-succinimidyl S-acetylthioacetate or N-succinimidyl S-acetylthiopropionate, can be dissolved in DMSO. The heterobifunctional linker solution can then be mixed with a solution that includes the antibody at a ratio of heterobifunctional linker and antibody of about 10:1, 15:1, 20:1, 25:1 or more to react the N-succinimidyl group with an amine of a lysine residue of the antibody and conjugate the heterobifunctional linker to the antibody.

In some, where the heterobifunctional linker includes a protecting group, such as an acetyl group coupled to a sulfhydryl group, the protecting group can be removed prior to reaction of the sulfhydryl group with the surface of the exposed portion of the working electrode using a deacetylation process. The deacetylation process can employ, for example, a hydroxylamine solution that is applied to the antibody.

Following conjugation of the heterobifunctional linker to the antibody and optionally removal of the protecting group, the antibody can be conjugated to surface of the working electrode. A chemical cleaning procedure can initially be applied to remove any oxides and particles on the working electrode surface to decrease the electrode charge transfer resistance. Typically, a sensor with the exposed working electrode can be immersed in an alkaline solution (e.g., 2M KOH solution), a first acidic solution (e.g., 0.05M $H_2SO_4$ solution), and a second acidic solution (e.g., 0.05M $HNO_3$ solution) different than the first acidic solution in sequence. The sensor can be immersed in DI water between immersion in each solution.

The linked antibody can then be applied to the surface of the working electrode using a micro-flow incubation system to link the antibody to the working electrode surface. Continuous flow incubation process can maximize the surface coverage of the antibody and enhance the homogeneity and reproducibility of the incubation results compared with static dropping incubation. The flow rate can be set at about 10 µL/min, 20 µL/min, 30 µL/min, 40 µL/min, 50 µL/min, 60 µL/min, 70 µL/min, 80 µL/min or more with a retention time for effective to allow reaction of the sulfhydryl group of the linker with the working electrode surface.

Following addition and linking of an antibody to the working electrode, the working electrode surface can be blocked using a blocking agent to minimize any non-specific molecule (e.g., protein) bonding on the electrode surface. This step will enhance the reproducibility and sensitivity of the biosensor. In some embodiments, DTT (Dithiothreitol), casein, and/or other blocking agents can be used to cover the open surface area of the working electrode and minimize any non-specific protein coverage.

In other embodiments, a plurality of biosensors can be provided on a surface of a substrate to provide a biosensor array. The biosensor array can be configured to detect analyte concentration changes in a host of chemical and/or biological processes (chemical reactions, cell cultures, neural activity, nucleic acid sequencing processes, etc.) occurring in proximity to the array. The biosensor array can include a plurality biosensors arranged in a plurality of rows and a plurality of columns. Each biosensor comprises a working electrode, a counter electrode, and a dielectric layer covering a portion of the working electrode and counter electrode and defining an aperture exposing other portions of the working electrode and counter electrode. Antibodies for an analyte of interest can be linked or conjugated to the working electrode as described herein. The antibodies can be the same or different for each biosensor of the array and can bind selectively to the analyte. The biosensors of the array can be configured to provide at least one output signal representing the presence and/or concentration of analyte proximate to a surface of the array. For each column of the plurality of columns or for each row of the plurality of rows, the array further comprises column or row circuitry configured to provide voltage potentials to respective biosensors in the column or row. Each biosensor in the row or column can potentially detect a different analyte and/or biased to detect different analytes.

Example 1

A bioconjuation technique was used for the preparation of a TDP-43 biosensor. Bioconjugation is a chemical strategy for forming a stable covalent link between a biomolecule and organic molecule, resulting in a zero length linkage between an antibody and electrode. This bioconjugation technique was used for the preparation of biosensor with the advantages on shortening the preparation process, enhancing the coverage of sensor surface/minimizing pinhole effect, and improving the practical usage for clinical application. Antibody and antigen interaction is still the crucial mechanism for ensuring the selectivity of the biosensor. N-succinimidyl S-acetylthioacetate (SATA) was used in preparation of antibody-enzyme conjugates. SATA was selected to conjugate monoclonal anti-TAR DNA-binding protein 43, which formed a SATA-acetylated antibody. Through the reaction between the SATA-acetylated antibody and hydroxylamine, a thiol labeled monoclonal anti-TAR DNA-binding protein 43 was produced and then applied onto gold sensor forming the gold-sulfur (Au—S) bond. Compared with complex multiple-day preparation processes of most biosensors on detection biomarkers, this unique procedure was a single step process. Combining this bio-conjugation preparation process with thin gold film biosensor and differential pulse voltammetry (DPV) as the transduction mechanism, a single-use, effective, sensitive and cost-effective biosensor for the detection of TDP-43 was successfully developed.

Methods

Materials and Apparatus

Human TDP43 peptide (Cat. ab41970) was purchased from Abcam (Cambridge, Miss.). Monoclonal Anti-TAR-DBP antibody produced in mouse (Cat. WH0023435M1), phosphate-buffer saline (PBS) 1.0 M (pH 7.4), undiluted human serum, ethylenediaminetetraacetic acid (EDTA) (Cat. EDS), dimethyl sulfoxide (DMSO), Amicon ultra-15 10K and amicon ultra-0.5 10K filters were purchased from Sigma Aldrich (St. Louis, Mo.). N-succinimidyl S-acetylthioacetate (SATA) (Cat. PI26102), potassium hydroxide pellets, concentrated $H_2SO_4$ (95.0 to 98.0 w/w %), and concentrated $HNO_3$ (70% w/w %) were obtained from Fisher Scientific (Pittsburgh, Pa.). A CHI 660C) Electrochemical Workstation (CH Instrument, Inc., Austin, Tex.) was used for DPV and EIS investigations. Time-of-Flight Secondary Ion Mass Spectroscopy (TOF-SIMS) was performed with a Physical Electronics TRIFT V nanoTOF TOF-SIMS (Chanhassen, Minn.).

Expression and Purification of the hnRNP F Protein

In order to evaluate the reaction mechanism of SATA with protein, a construct that contains the N-terminal domain of the hnRNP F protein (FqRRM12) was used since the amide NMR signals of the lysine residues were already characterized. The DNA sequence encoding the FqRRM12 (residues from 1 to 194) was cloned into the NdeI/EcoRI site of the pMCSG7 vector containing an N-terminal hexa-histidine tag and TEV protease cleavage site. FqRRM12 was overexpressed in BL21(DE3) cells and uniformly labeled with $^{15}N$-labled ammonium chloride as the only nitrogen source in the M9 minimum medium. Cells were cultured at 37° C. to an optical density at 600 nm of ~0.6-0.8 and induced by adding Isopropyl-B-D-thiogalactopyranoside (IPTG) to a final concentration of 1 mM. The BL21(DE3) cells were grown overnight after induction and centrifuged. Cell pellets were resuspended in lysis buffer (50 mM $Na_2HPO_4$, 1M NaCl and 20 mM Imidazole, pH 7.5), and lysed by sonication. Cell lysates were centrifuged 15 minutes at 16,000 g. FqRRM12 was purified using Roche Complete His-Tag purification column and TEV protease was added to cleave the His-tag. The Tev cleaved FqRRM12 was further purified by size exclusion chromatography using the HiPrep16/60 sephacryl S-100 column with NMR buffer (25 mM $NaH_2PO_4$, 50 Mm NaCl and 4 mM TCEP, pH 6.2) and concentrated to 0.4 mM (qRRM12). NMR $^{15}$N-$^1$H HSQC experiments were carried out at 298K using a Bruker 800 MHz spectrometer equipped with a cryoprobe. Data were processed with NMRpipe and further analyzed with Sparky. Chemical shift assignments of the backbone amide groups were transferred from the previously reported studies.

The produced FqRRM12 protein was then used to react with SATA in order to evaluate the effectiveness of SATA/protein bioconjugation mechanism. 7 mg SATA was firstly dissolved in 0.5 mL DMSO. 10 µL of SATA solution was mixed with 400 µL of protein in 0.1 M PBS solution based on a molar ratio between SATA and antibody of 9:1. Solution was mixed with vortex and incubated at 25° C. for 30 minutes. The acetylated protein was then purified by running a desalted column with PBS buffer and the protein was characterized by 1H-15N NMR HSQC, as shown in the results part. The deacetylation process aimed at generating the sulfhydryl group linked protein by the reaction with a prepared deacetylation solution (0.5 M hydroxylamine, 25 mM EDTA in 0.1M PBS solution with pH at 7.2). EDTA was added during the reaction preventing crosslinking between the sulfhydryl groups. 40 µL of the deacetylation solution was mixed with 400 µL modified protein solution and incubated for 2 hrs at 25° C. The thiol-linked protein was then purified by running a desalted column with PBS buffer containing 10 mM b-mercaptoethanol and the protein was characterized by $^1$H-$^{15}$N NMR HSQC, as shown in the results part. After the NMR evaluation, protein was recovered by transferring the solution to Amicon ultra-15 10K filter. The thiol-linked protein was diluted to 14 mL with EDTA buffer and centrifuged at 12000 rpm for 10 minutes at 10° C. to concentrate the protein solution to 400 µL. Previous step was repeated for 3 times to obtain 400 µL sulfhydryl modified protein. The concentration of the sulfhydryl modified protein solution was determined by UV light at 280 nm to be 1.72 mg/mL in 0.1 M PBS with 25 mM EDTA solution. The product was stored at 4° C. for future use.

Synthesis of Thiol-Linked Anti-TAR DNA-Binding Protein 43 (Anti-TDP-43)

Figure 2:
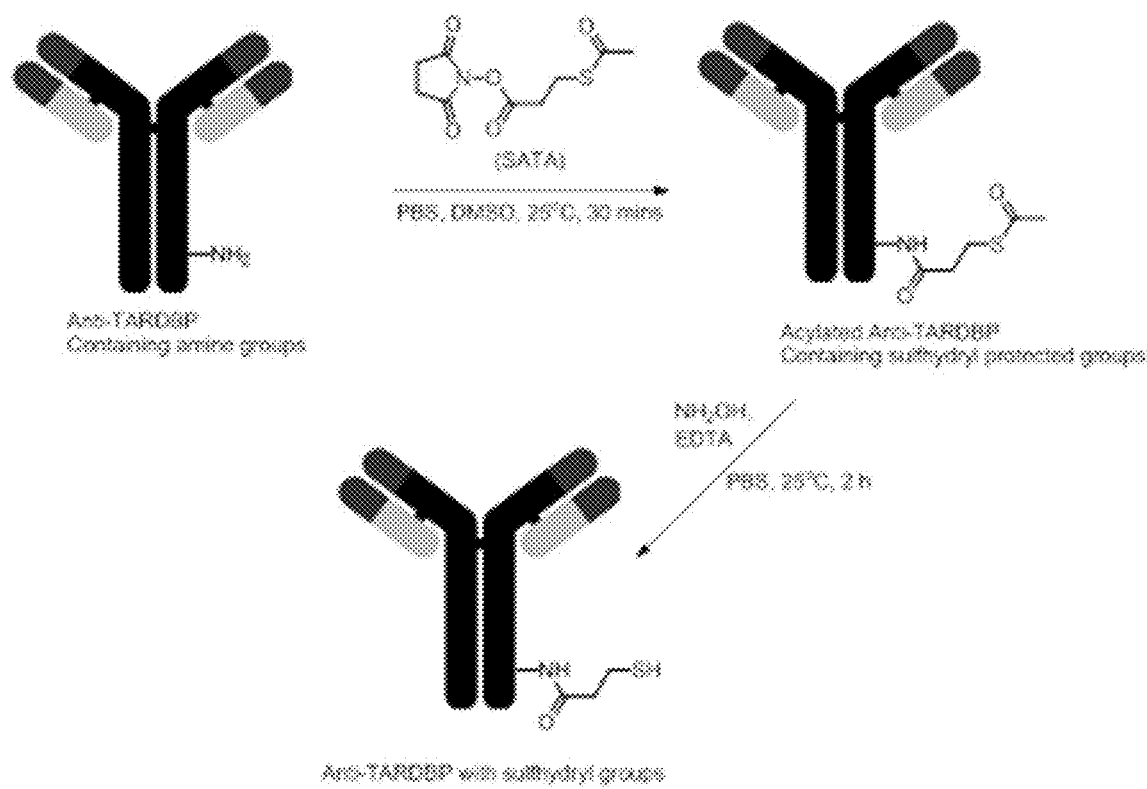
FIG. 2 illustrates free primary amine groups on anti-TARDBP react with SATA to generate acylated anti-TAR-DBP contain thioester groups. After treatment with hydroxylamine, thioester groups hydrolyze to sulfhydryl groups. EDTA was added during the reaction to prevent crosslink between sulfhydryl groups.

Thiol-linked anti-TAR DNA-binding protein 43 was synthesized for further use for the biosensor fabrication. 0.5 mg of SATA was firstly dissolved in 1 mL of DMSO. 1 µL of the prepared SATA solution was mixed with 50 µL of anti-TAR DNA-binding protein 43 product in 0.1M PBS solution based on a molar ratio between SATA and antibody of 20:1, and incubated together for 30 min at room temperature. The solution was then filtered by Amicon ultra-0.5 10k filter. The filtered solution was diluted to 0.5 mL with 0.1M PBS and centrifuged at 12000 rpm for 15 min at 10° C. producing a concentrated modified antibody sample of a total volume of 50 µL. This filtered antibody solution was stored at 4° C. condition and ready for further deacetylation process. The deacetylation process aimed at generation of sulfhydryl group linked protein by the reaction with a prepared deacetylation solution (0.5M hydroxylamine, 25 mM EDTA in 0.1M PBS solution with pH at 7.2). 5 µL of the deacetylation solution was mixed with 50 µL filtered antibody solution and incubated for 2 hrs at room temperature. Amicon ultra-0.5 10k filter was applied again, and the deacetylated antibody solution was diluted to 0.5 mL with 10 mM EDTA in 0.1 M PBS solution and centrifuged at 12000 rpm for 15 min to a volume of 50 µL. This dilution process was repeated for 3 times to remove excessive reagents. Thiol-linked anti-TAR DNA-binding protein 43 was produced through this process. The produced thiol-linked antibody was then used for TDP-43 biosensor fabrication. FIG. 2 shows the synthesis process described above.

Quantitatively, the concentration of the produced thiol-linked protein was determined by the absorptivity at 280 nm by ultraviolet light. As shown in table 1, the concentration of the produced thiol-linked antibody was at 0.12 mg/mL.

TABLE 1

| Concentration profile of the thiol-linked Anti-TDP43 | | | |
|---|---|---|---|
| | Volume (µL) | Abs. at 280 nm | Conc. (mg/mL) |
| Antibody as purchased | 20 | 0.221 | 0.5 |
| Antibody in PBS buffer before reaction | 50 | 0.083 | 0.19 |
| Antibody with —SH group | 50 | 0.052 | 0.12 |

Preparation of TAR DNA-Binding Protein 43 (TDP-43) Biosensor Using a Micro-Flow Incubation System A chemical cleaning procedure was applied to remove any oxides and particles on the biosensor surface to decrease the electrode charge transfer resistance. Typically, a row of 8-10 biosensors were immersed individually in 2M KOH solution, 0.05M $H_2SO_4$ solution (95.0 to 98.0 w/w %), and 0.05M $HNO_3$ solution (70 w/w %) in sequence for 5 min each. The row of biosensors was rinsed by DI water between each cleaning solution. After cleaning, nitrogen air was used for drying the biosensor. The effectiveness of this cleaning process was proved in a previous study. Prepared thiol-linked anti-TDP-43 (Anti-TARDBP43) solution was then diluted by 0.1M PBS buffer with 10 mM EDTA and 0.15 M NaCl to a concentration of 0.25 µg/mL. A micro-flow incubation system was applied for incubation of thiol-linked antibody solution. Continuous flow incubation process can maximize the surface coverage of protein and enhance the homogeneity and reproducibility of the incubation results comparing with static dropping incubation. The continuous flow system was made with stainless steel and designed to accommodate 10 biosensors inside the flow system. The flow rate was set at 80 µL/min with a retention time for 3 hours at 4° C. After incubation, the biosensors were rinsed with 0.1 M PBS and dried with nitrogen gas and stored at 4° C.

Results

NMR Analysis of SATA Modified FqRRM12 Protein

Figure 3A:
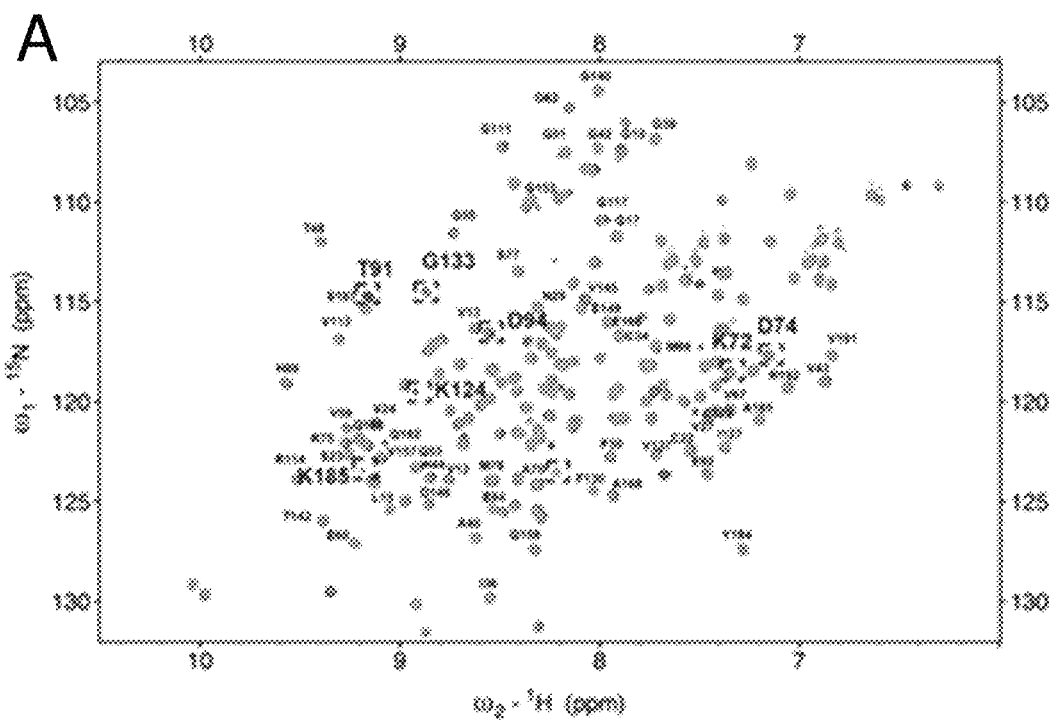
FIGS. 3(A-D) illustrate (A) Overlay $^1H$-$^{15}N$ HSQC spectrum of FqRRM12 and acetylated FqRRM12. (B) Possible locations of amino acids modified by SATA on the 3D structure of FqRRM12. Chemical shift perturbations to D74 and G133 were also detected upon SATA modification, likely due to their close proximity to K171 and K72. (C) Overlay $^1H$-$^{15}N$ HSQC spectrum of SATA-acetylated FqRRM12 and SATA modified FqRRM12 with reduced thiol groups. (D) Nyquist plot presents the impedance differences between cleaned bare electrode and sulfhydryl modified protein bonded electrode.
Figure 3B:
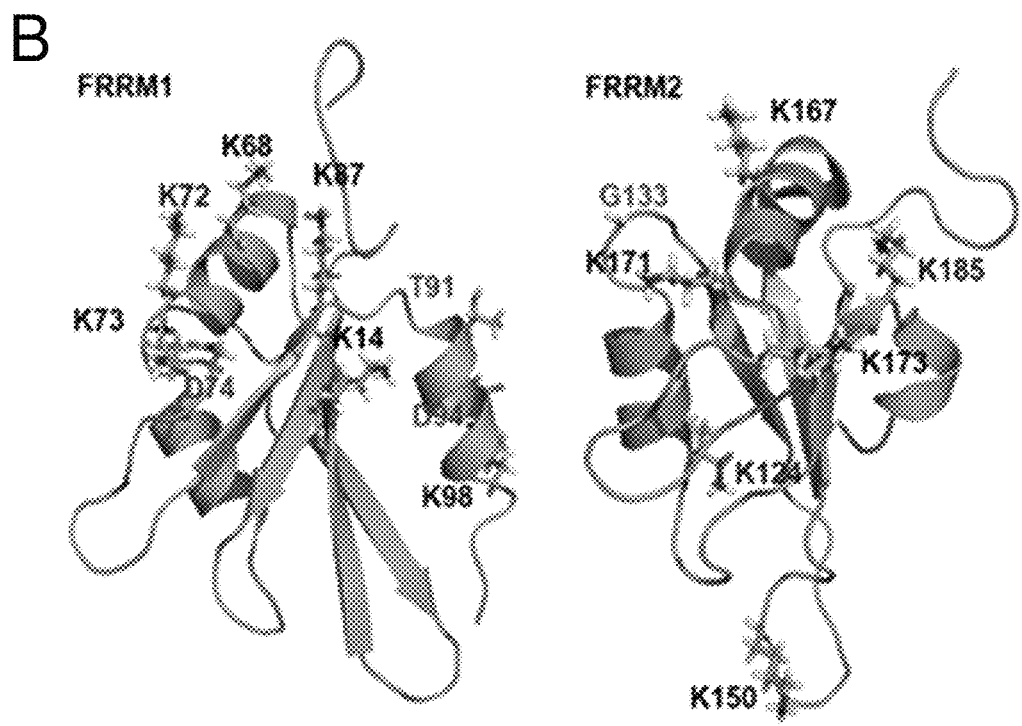

In order to examine the efficiency of sulfhydryl modification, a protocol to monitor the extent of modification by NMR spectroscopy was developed using the N-terminal fragment of the hnRNP F protein (FqRRM12) as a model system. The $^{15}$N-$^1$H Heteronuclear Single Quantum Coherence ($^{15}$N-$^1$H HSQC) spectrum of a $^{15}$N-labeled protein reports on the chemical environment of each amide group within a protein, and as such it provides a convenient analytical tool to monitor post-translational modifications. Sulfhydryl modification is a classical type of lysine acetylation; therefore, we followed the reaction of FqRRM12 with SATA by comparing HSQC spectra of the unmodified and modified $^{15}$N-labeled protein. FIG. 3A shows the overlay of the $^{15}$N-$^1$H HSQC spectra of unmodified and modified FqRRM12. Comparison of the spectra reveal that the correlation peaks of Lys72, Lys124 and Lys185 completely disappear in the SATA-modified protein. Interestingly, the signal intensity of Gly133 and Asp74 were also significantly reduced in the $^{15}$N-$^1$H HSQC spectrum as shown in FIG. 3A. Analysis of the FqRRM12 three-dimensional structure (PDB ID: 2kfy; 2kg0) shows that Gly133 and Asp174 are in close proximity to the side chains of Lys171 and Lys72, respectively as shown in FIG. 3B, which might account for the observed perturbations to their correlation peaks. Of note, SATA modification of the epsilon amine groups of lysine residues result in formation of new amide bonds that should be detected by NMR. Indeed, the $^{15}$N-$^1$H HSQC spectrum of SATA modified FqRRM12 shows additional correlation peaks relative to the unmodified protein as shown in FIG. 3A.

Figure 3C:
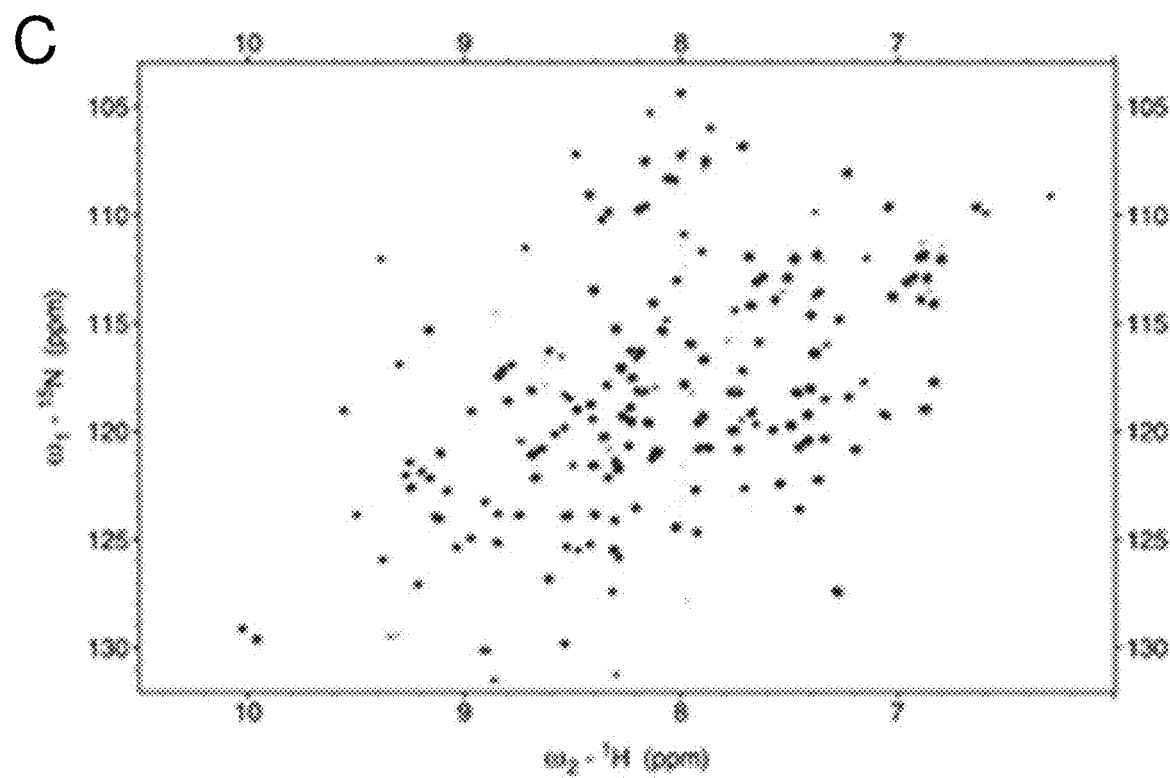
Figure 3D:
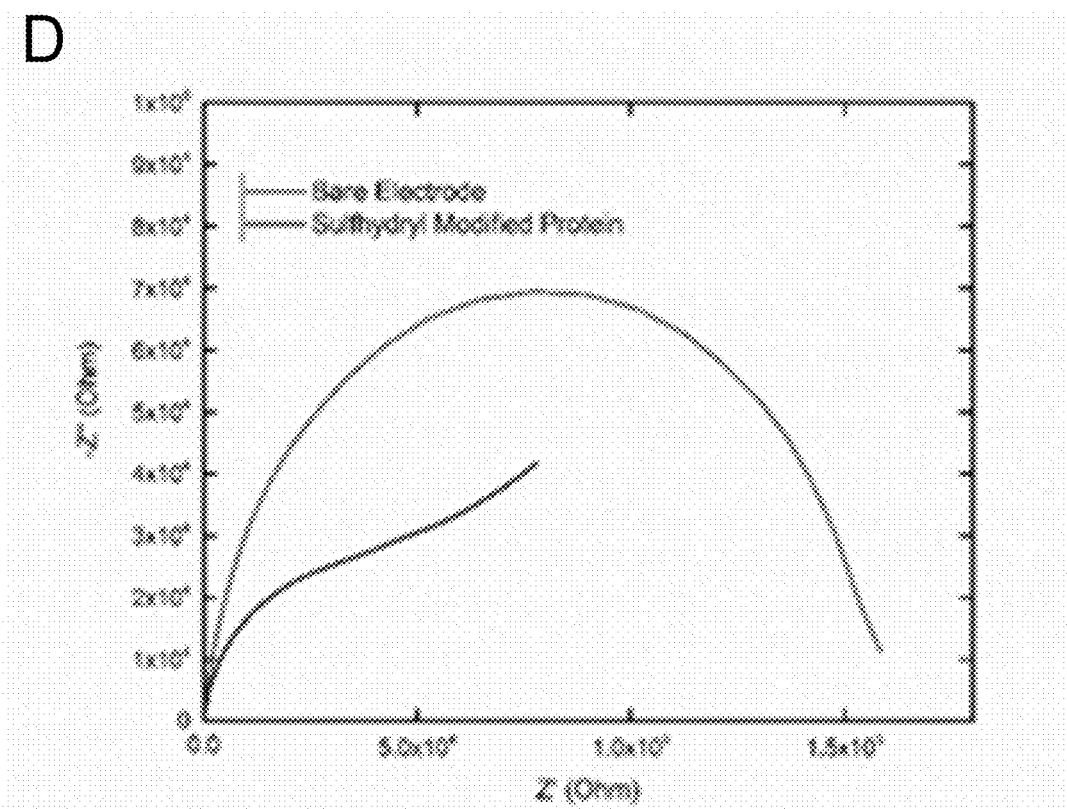

The second step of the chemical reaction, which reduces the attached SATA to a thiol functional group, was also monitored by recording $^{15}$N-$^1$H HSQC experiments. Comparison of the spectra of the oxidized and reduced forms of the SATA modified FqRRM12 reveal that the reduction occurs site-specifically since the NMR chemical shifts of the two proteins are essentially identical as shown in FIG. 3C. The absence of additional chemical shift perturbations to FqRRM12 upon reducing SATA is expected given that the site of reaction is more than four bonds away from the amide group. Furthermore, electrochemical impedance spectroscopy (EIS) was conducted to confirm the existence of sulfhydryl modified FqRRM12 by examining the ability of the modified protein to bind with gold electrode surface. After incubation of 5 μg/mL of the modified FqRRM12 for 1 hour on the gold sensor, EIS test was applied using 20 μL of a solution with 5 mM in each component of $K_3Fe(CN)_6$ and $K_4Fe(CN)_6$, and significant impedance difference was observed comparing with the impedance on the bare electrode using the same redox solution. In FIG. 3D, the line represents the surface impedance from the sulfhydryl modified FqRRM12 produced electrode and the black line represents the surface impedance from a cleaned bare electrode. Taken together, the NMR and EIS results confirm that FqRRM12 is site-specifically modified under our experimental conditions.

Figure 4A:
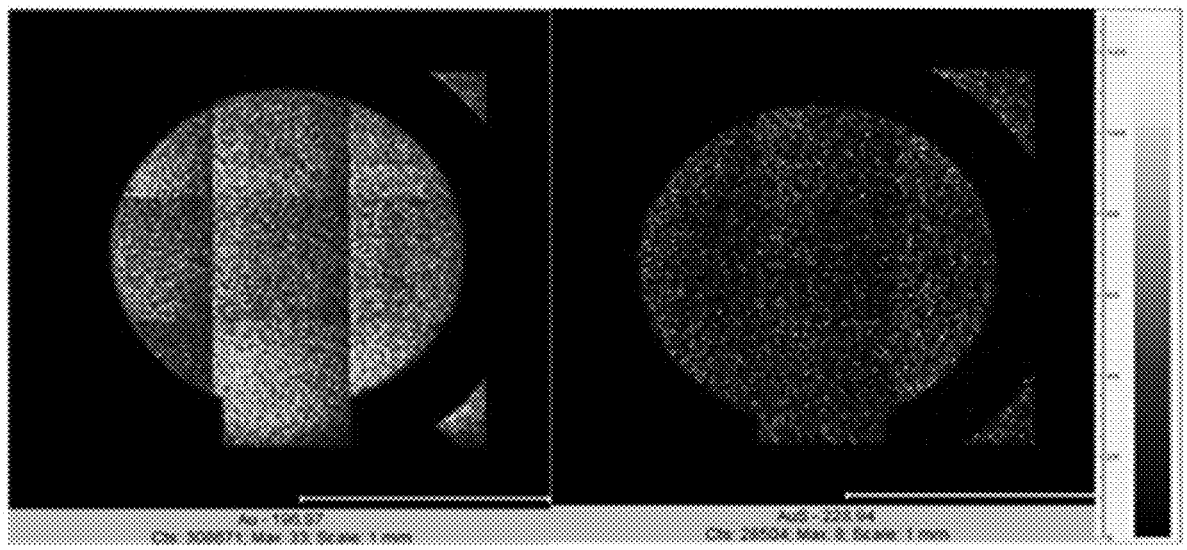
FIGS. 4(A-B) illustrate (A) the total secondary ions acquired at the negative polarity of gold (left) and gold-sulfur ion image (right) using a $Ga^+$ primary source for thiol-linked Anti-TDP43 covered electrode. (B) The total secondary ions acquired at the negative polarity of gold (left) and gold-sulfur ion image (right) using a $Ga^+$ primary source for 11-MUA linked Anti-TDP43 formed monolayer.
Figure 4B:
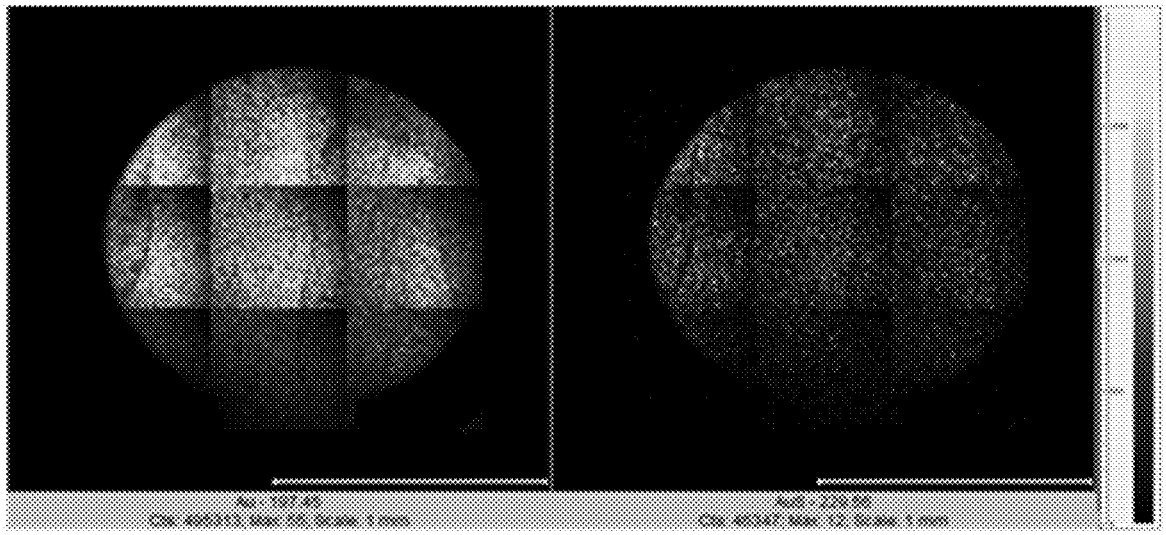

Time-of-Flight-Secondary Ion Mass Spectrometry (TOF-SIMS) Analysis of Thiol-Linked Antibody Coverage In order to confirm the effectiveness of the SATA and protein reaction for the practice of biosensor fabrication, the validity of gold sulfur (Au—S) bond and the coverage of the working electrode surface were investigated by TOF-SIMS technique. The working electrode with linked anti-TAR DNA binding protein 43 (anti-TDP43) were used for analysis. Two biosensors prepared separately by thiol linked anti-TDP43 and traditional 11-Mercaptoundecanoic acid (11-MUA) formed monolayer with cross-linked anti-TDP43 were analyzed and the electrode coverage of each sample was compared. TOF-SIMS was performed under negative polarity to use the better sensitivity of the instrument to Au, S and their fragments. Element maps for Au and Au—S demonstrated the distribution with a primary source of both C60 and Ga ions. The images acquired with Ga source were selected to show the electrode coverage with better spatial resolution. Experimentally, the primary source was a $Ga^+$ beam accelerated to 30 KV and bunched to a pulse size of 7 ns and an acquisition rate of 8 KHz. At this setting, the surface of the electrode was mapped with a spatial resolution of 500 nm. Map stitching was then used to generate ion maps with a total area of 2×2 mm. The confirmation of Au—S bond on the gold electrode surface indicated the successful synthesis of thiol-linked protein as shown in FIG. 4A. FIG. 4B shows the coverage of Au—S bond of the electrode using 11-MUA prepared monolayer with cross-linked antibody. The difference in coverage between the two samples was apparent. The counts percentage of Au—S bond based on total counts in the developed thiol-linked anti-TDP43 electrode was 63.3% higher comparing to that of the 11-MUA linked antibody covered electrode. The results of TOF-SIMS analysis proved the effectiveness of bioconjugation mechanism's ability of efficiently covering electrode surface, ensuring the reproducibility of further antigen incubation and detection.

Detection of TAR DNA-Binding Protein 43 in Phosphate Buffer Saline (PBS) and Undiluted Human Serum Differential pulse voltammetry (DPV) was used as the transduction mechanism for the detection of TDP-43 in this study. Compared with common electrochemical voltammetry, such as cyclic voltammetry, differential pulse voltammetry applies pulse potential following with a potential drop and an immediate measurement of current outputs, in which the charge current is minimized and the sensitivity of the measurement is enhanced. PBS prepared TDP-43 antigen was used for testing. Human recombinant TDP-43 antigen was diluted by 0.1M PBS solution to multiple concentrations ranging from 1 μg/mL to 0.01 μg/mL. The 20 μL of prepared antigen solution was then applied onto the prepared biosensors. The incubation time of TDP-43 antigen was 1 hour at room temperature. After incubation, each biosensor was rinsed by 1 mL 0.1M PBS solution and dried by nitrogen. Before testing, 20 μL of a redox probe solution with 5 mM in each component of $K_3Fe(CN)_6$ and $K_4Fe(CN)_6$ was applied onto the biosensor, and the current output through the DPV measurement was used to quantify the concentration of TDP-43 antigen in 0.1M PBS solution. A voltage ranges of −0.25 V to +0.35 V was applied for DPV measurement. FIG. 4A shows the DPV measurement for PBS prepared antigen. Electrochemical impedance spectroscopy was also conducted to measure the surface impedance in order to verify the detection result from DPV for PBS test. As shown in FIG. 4B, the highest concentration indicates the highest impedance (biggest circle) on the sensor surface at low frequency region, which was consistent with the highest current output through the DPV measurement.

The performance of this bioconjugation mechanism fabricated TDP-43 bio sensor was compared to that of a commonly prepared method fabricated TDP-43 biosensor using 11-Mercaptoundecanoic acid (11-MUA) as monolayer to covalently immobilize antibody for the detection of antigen. The antigen incubation time and the concentration range for PBS test were remained identical for examination of both types of biosensors. The current outputs of the commonly prepared biosensor were at the level of $10^{-6}$A in DPV measurement, which was 10 times lower than that of bioconjugation method prepared TDP-43 biosensor, indicating a better sensitivity for the bioconjugation mechanism fabricated TDP-43 biosensor.

Figure 5A:
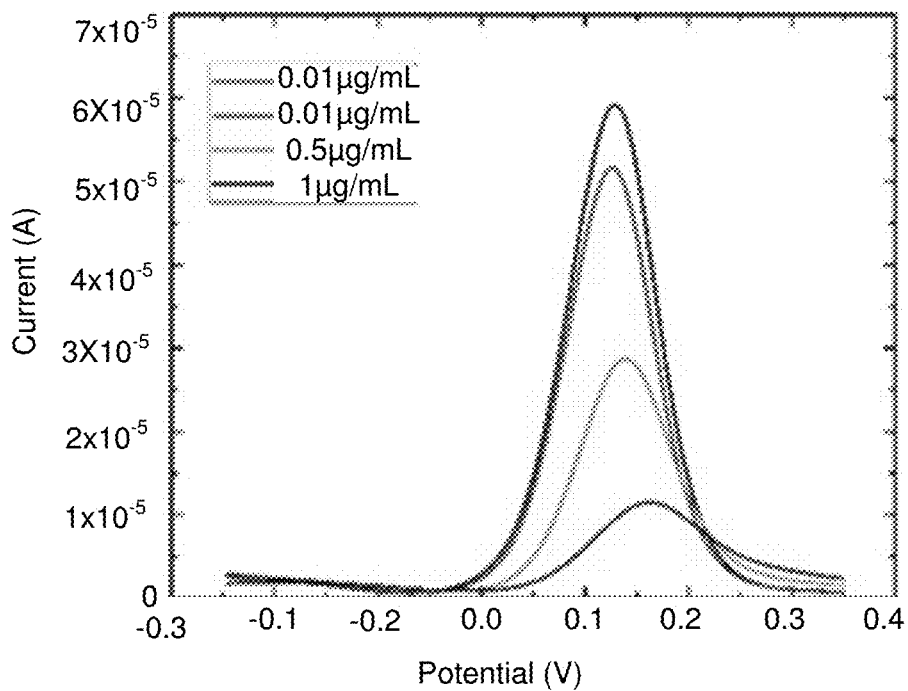
FIGS. 5(A-D) illustrate (A) DPV measurement of TDP-43 antigen in 0.1M PBS solution. (B) Nyquist Plot of TDP-43 antigen in 0.1M PBS solution. (C) Calibration linear curve based on DPV measurement of TDP-43 antigen in undiluted human serum. (D) DPV measurement of TDP-43 antigen in undiluted human serum with limitation and interference tests.
Figure 5B:
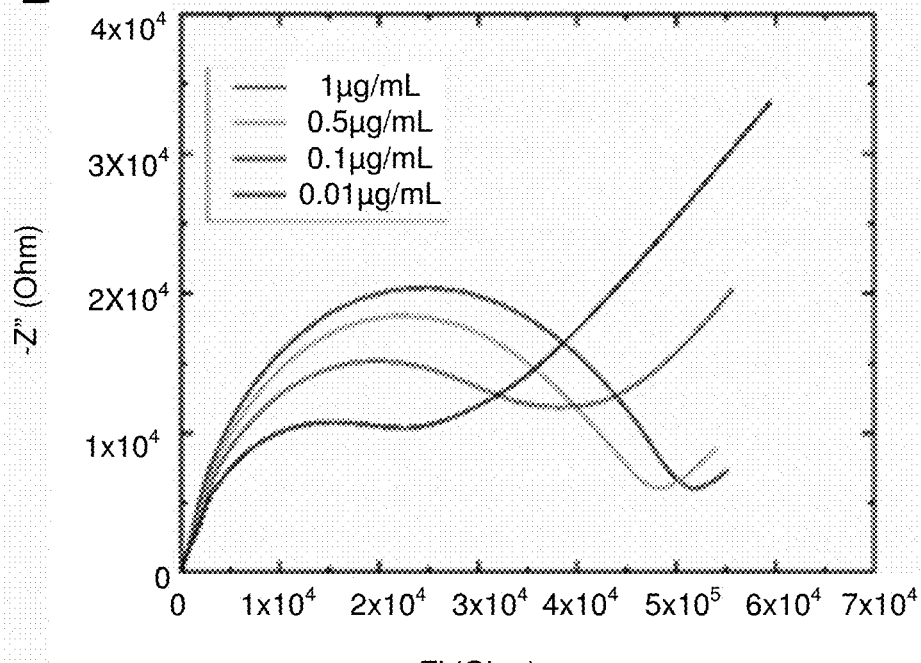
Figure 5C:
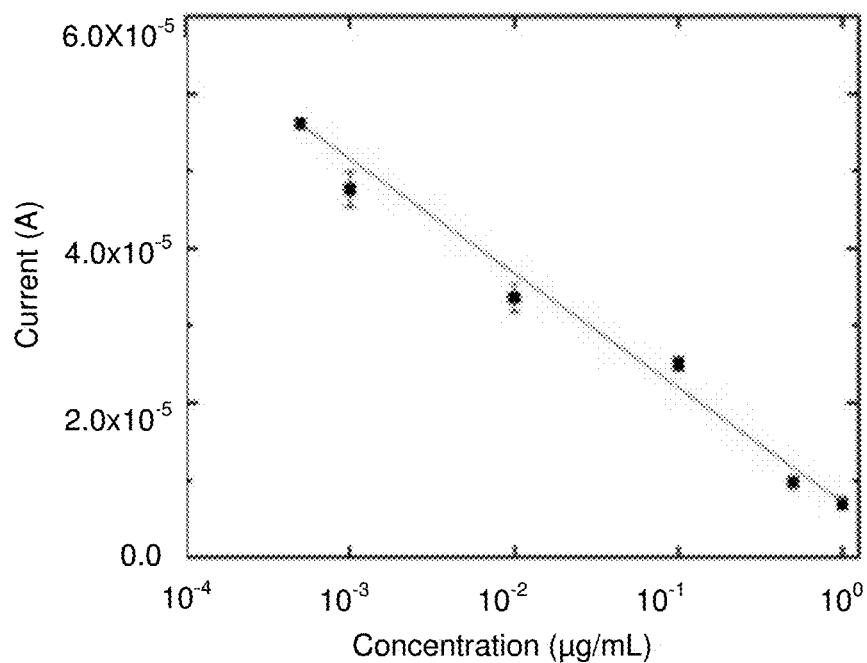

Human recombinant TDP-43 antigen was also diluted by undiluted human serum to multiple concentrations, ranging from 0.0005 μg/mL to 1 μg/mL. The procedure for TDP-43 antigen in PBS measurement was also used in the serum test for DPV measurement. The calibration curve for the DPV measurement is shown in FIG. 5C with a linear relationship of $Y=-1.5\times10^{-5} X+7.2\times10^{-6}$ with a R-square value of 0.986, indicating a high reproducibility with n>5.

Figure 5D:
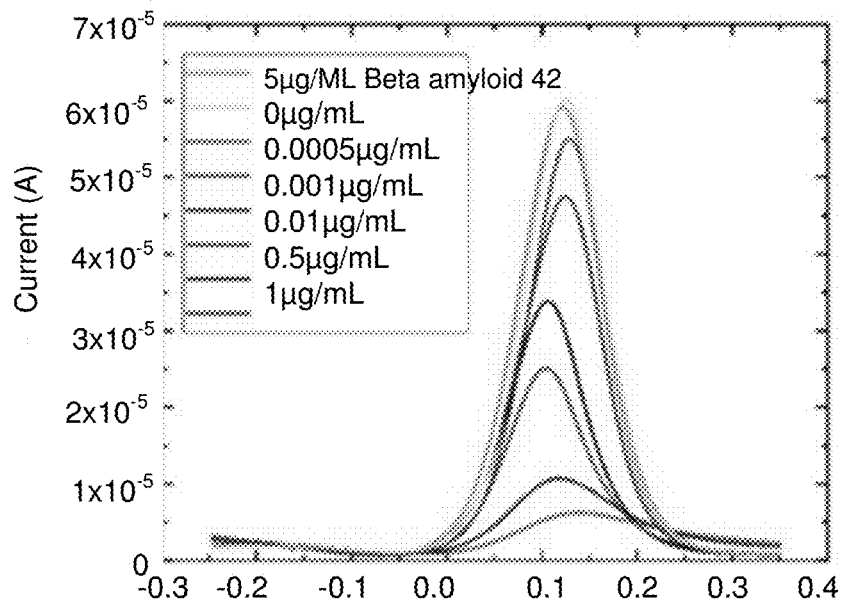

From the serum detection test, the limitation of detection of TDP-43 antigen was found at 0.0005 µg/mL (dark line) in FIG. 5D, which aligned closely to the zero concentration line (light line). In order to confirm the selectivity of this developed TDP-43 biosensor, antigen was selected for interference test of this biosensor. 5 µg/ml of β-amyloid 42 antigen solution in human serum was incubated onto the TDP-43 biosensor for 1 hour at room temperature. The current output based on the detection procedure is shown as the color line in FIG. 5D, which overlapped with the detection response of non-TDP-43 antigen solution. Another interference test was conducted by a mixed solution of 5 µg/ml of β-amyloid 42 with 0.1 µg/ml of TDP-43 antigen. The mixed solution was incubated on the TDP-43 biosensor for one hour. The current output of DPV measurement of this mixed solution was identical to the current output of DPV measurement of only 0.1 µg/ml of TDP-43 antigen as the line signal in FIG. 5D. These two tests confirmed an excellent selectivity of the TDP-43 biosensor.

A simple-prepared, cost-effective biosensor for the detection of TAR DNA-binding protein 43 (TDP-43) was designed, fabricated and evaluated by the detection of TDP-43 antigen in PBS solution and undiluted human serum with a detection concentration range of 0.0005 µg/mL to 1 µg/mL using differential pulse voltammetry (DPV). A good reproducibility and sensitivity were shown by multiple electrochemical tests. Selectivity was confirmed by using β-amyloid 42 antigen as a potential interference biomolecule, producing no signal interference. The bioconjugation technique used in this example demonstrated a time-efficient and effective method for fabrication of this biosensor. The effectiveness of this bioconjugation mechanism on producing thiol-linked protein was confirmed by the evaluation of FqRRM12 Protein. Overall, the preparation of this TDP-43 biosensor required total of three hours. The test of TDP-43 antigen sample required one hour of incubation, and 30 seconds for DPV measurement. This biosensor system can be applied for detection of other biomarkers in neurodegenerative disorders or other diseases.

Example 2

Self-assembled monolayer (SAM) was a promising platform technology for biosensor applications. Typically, self-assembled monolayer formed by alkane linked thiol molecule produced a gold-sulfur (Au—S) bond with a gold electrode surface of a biosensor. Then, an activation of the terminal functional group was followed, immobilizing to an antigen binding, such as antibody, aptamer and specific receptor. The formation of the gold electrode elements, working and counter electrodes, of the biosensor could be accomplished by various techniques and in different dimensions. In this example, the gold electrode elements were thin gold film, 50 nm in thickness, and was deposited by sputtering physical vapor deposition (PVD) on a roll-to-roll cost effective manufacturing method producing the biosensor relatively inexpensively and effectively. This biosensor was a three electrode configuration. For a comprehensive development of this biosensor, six different SAMs were studied, compared and assessed in this research. These general preparing procedures of commonly used biosensor were complex and required days for the preparation and consumed excess chemicals. Furthermore, the biosensors used SAMs had relative low sensitivity and poor reproducibility, due to common monolayer defects, such as pinholes, inhomogeneity of surface coverage and others. Therefore, a new technique for the preparation of biosensor was used in this study, and it was the bioconjugation mechanism.

Bioconjugation mechanism conjugates two or more molecules forming a novel complex embracing the combined properties of its individual components. This results in a zero length linkage between protein and electrode elements of the biosensor. Furthermore, this bioconjugation technique will shorten the preparation process, enhance the coverage of the biosensor surface/minimizing pinhole effect. Consequently, this will improve the practical clinical application. The interaction between antibody and antigen remained to be the biorecognition mechanism in this research endeavor. In this example, anti-AMACR and anti-PSA were modified by bioconjugation technique using N-succinimidyl S-acetylthioacetate (SATA) to conjugate the antibody. The final product of the conjugation reaction was a thiol group linked AMACR antibody or PSA antibody, which directly linked with the thin gold film electrode element surfaces of the biosensor through incubation. After modified by thiol linked antibody, the fabrication of AMACR or PSA biosensor was completed. This single step preparation took approximately one day including the incubation time for the preparation of the biosensor.

Thus, the combination of bioconjugation technique in preparation, the microfabrication of thin gold film based biosensor prototype and the differential pulse voltammetry (DPV) measurement technique results in a single-use, cost effective and highly sensitive and selective biosensor for the detection of the biomarkers of prostate cancer, AMACR and PSA; a very attractive and practical diagnostic tool for the screening application of prostate cancer.

Materials

Anti-AMACR (Cat. No. HPA019527) was obtained from Sigma Aldrich (St. Louis, Mo., USA), and AMACR (Cat. No. MBS428004) was obtained from MyBioSource (San Diego, Calif., USA). Phosphate-buffer saline (PBS) 1.0 M (pH 7.4), human serum (Cat. No. H3667), DLDithiolthreitol solution (DTT) (Cat. No. 43816), 3-Mercaptopropionic acid (3-MPA) (Cat. No. M5801), 6-Mercapto-1-hexanol (6-MCH) (Cat. No. 451088), 11-Mercaptoundecanoic acid (11-MUA) (Cat. No. 450561), N-(3-dimethylaminopropyl)-N'-ethylcarbodiimide hydrochloride (EDC) (Cat. No. E1769), N-hydroxysuccinimide (NHS) (Cat. No. 130672) and NHydroxysulfosuccinimide sodium salt (Sulfo-NHS) (Cat. No. 56485) were purchased from Sigma-Aldrich (St. Louis, Mo., USA). N-succinimidyl S-acetylthioacetate (SATA) (Cat. #26102) and Dimethyl sulfoxide (DMSO) (Cat. #BP231-1) were obtained from Thermo Fisher Scientific (Pittsburgh, Pa. USA). Ethylenediaminetetraacetic acid (EDTA) (Cat. EDS) and Hydroxylamine (Cat. #255580) were obtained from Sigma Aldrich (St. Louis, Mo., USA) .Concentrated $H_2SO_4$ (95.0 to 98.0 w/w %), concentrated $HNO_3$ (70% w/w %) were received from Fisher Scientific (Pittsburgh, Pa., USA). Potassium hydroxide (KOH), Potassium ferricyanide (K3Fe(CN)6) and Potassium ferrocyanide (K4Fe(CN)6) (Cat. No. P1767, P3289 and P3667) were obtained from Sigma-Aldrich (St. Louis, Mo., USA). All the chemicals were used without further purification. A CHI 660C (CH Instrument, Inc., Austin, Tex., USA) Electrochemical Workstation was used for DPV characterization.

Experiments

Preparation of Self-Assembled Monolayer(SAM) Based Biosensor

Self-assembled monolayer (SAM) is pivotal for binding antibody. Different configurations of self-assembled monolayer affect the orientation of the antibody and the electrode surface coverage of the biosensor, resulting in various binding effects and current signal outputs for the electrochemical detection. Six different self-assembled monolayer systems were prepared examining their effectiveness in the surface preparation of the biosensor in this study. The configurations of the six SAM system are shown in Table 2. These SAM systems were prepared in ethanol solution. Thin gold film based biosensors were firstly cleaned as described in a previous study and immersed in the different SAM solutions for 24 hours at room temperature.

TABLE 2

Compositions of six different self-assembled monolayer systems

| SAM1 | SAM2 | SAM3 | SAM4 | SAM5 | SAM6 |
|---|---|---|---|---|---|
| 1 mM 3-Mercaptopropionic acid (3-MPA) | 1 mM 3-MPA and 0.13 mM DL-Dithiolthreitol (DTT) | 5 mM 11-Mercaptoundecanoic acid (MUA) | 1 mM MUA and 10 mM 6-Mercapto-1-hexanol (MCH) | 1 mM MUA and 10 mM 3-MPA | 3 mM MUA and 9 mM MCH |

Figure 6:
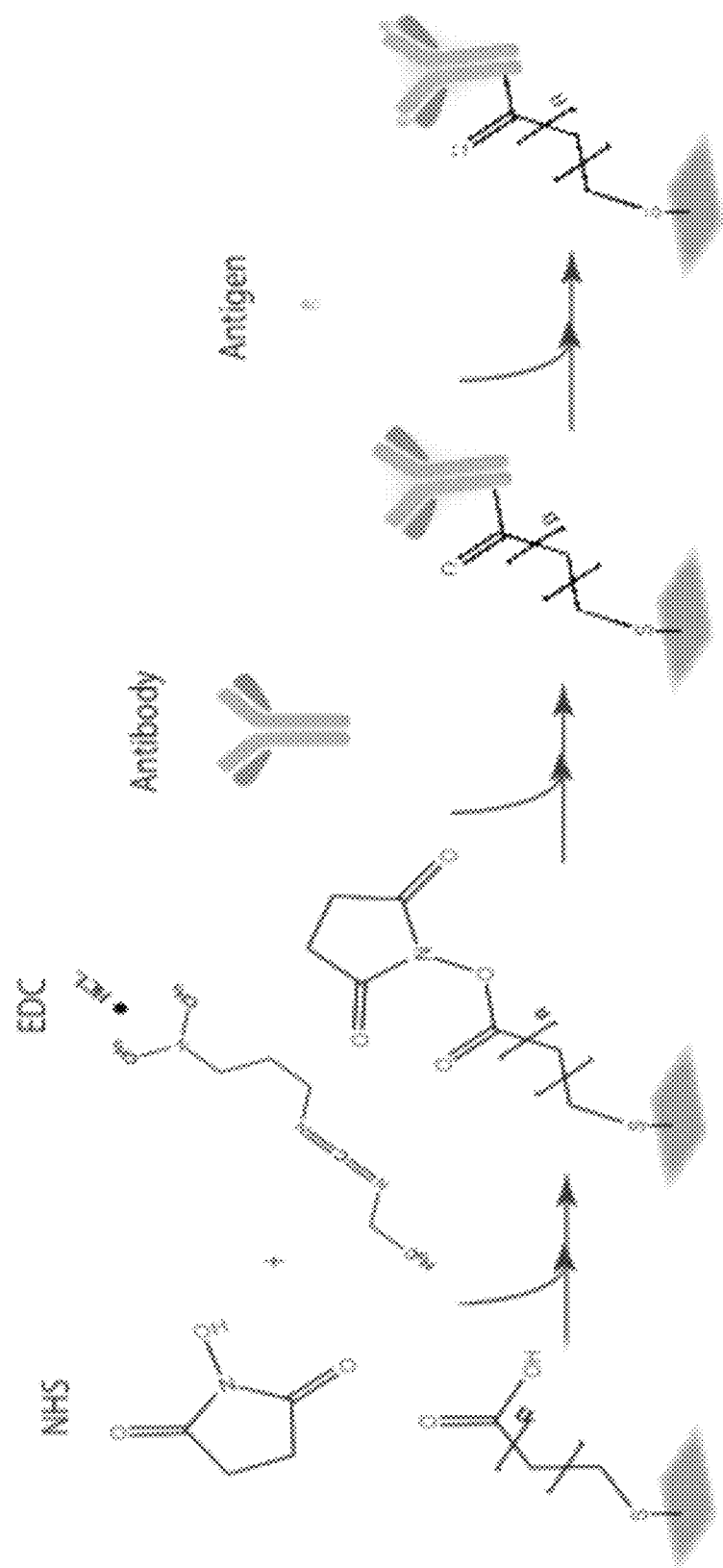
FIG. 6 illustrates SAM biosensor preparation process.

After 24 hours immersion in the SAM solution, the biosensors were rinsed by DI water and dried by nitrogen gas. 0.2 M of N-(3-dimethylaminopropyl)-N'-ethylcarbodiimide hydrochloride (EDC) and 0.05M of N-hydroxysuccinimide (NHS) in 0.1 M PBS solution were prepared to activate the carboxylate group on the SAM by immersing the biosensors in the prepared SAM solution for 1 hr at room temperature. Using anti-AMACR as an example, 20 µL of anti-AMACR solution with a concentration of 1 µg mL$^{-1}$ was drop-casted onto the biosensor after the activation process and incubated for 15 hrs at 4° C. The biosensor was then ready to be assessed for the effectiveness of the SAM system. The process of the fabrication of SAM biosensor is shown in FIG. 6.

Preparation of Thiol-Linked Anti-AMACR or Anti-PSA Protein

Figure 7:
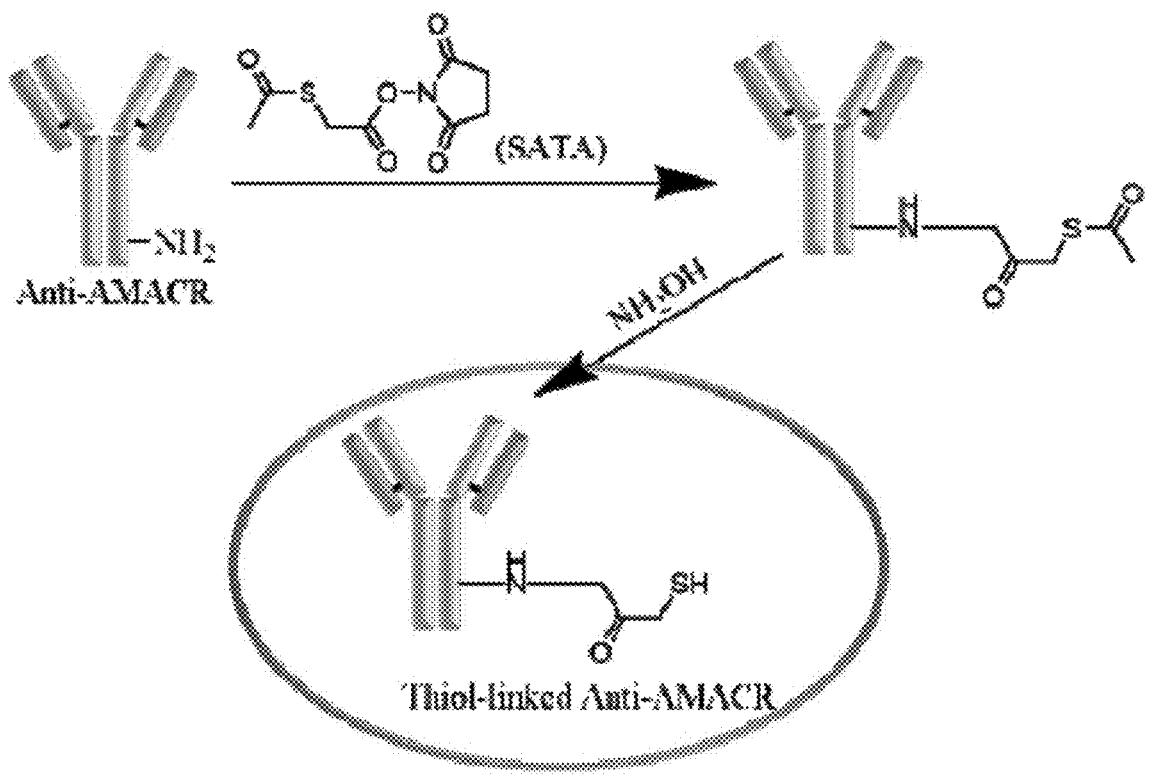
FIG. 7 illustrates the reaction mechanism of Anti-AMACR with SATA.

Bioconjugation mechanism was applied to create the thiol-linked anti-AMACR or anti-PSA protein. N-succinimidyl S-acetylthioacetate (SATA) was used to conjugate the antibody in order to produce a thiol-linked anti-AMACR or anti-PSA protein. Typically, for the preparation of the thiol-linked anti-AMACR, 0.5 mg of SATA was firstly dissolved in 1 mL of DMSO. 1 µL of the prepared SATA solution was mixed with 30 µL of anti-AMACR in 0.1M PBS solution based on a molar ratio between SATA and the antibody of 20:1[20]. This mixed solution was incubated for 30 min at room temperature. The solution was then diluted to a total volume of 500 µL by 0.1M PBS solution and transferred into an Amicon ultra-0.5 10k filter tube, centrifuging at 12000 rpm for 15 min at 5° C. 25 µL of the filtered solution was obtained, and this filtered solution was reacted with 5 µL of 0.5M hydroxylamine and 25 mM EDTA in 0.1M PBS solution at room temperature for 2 hrs. Amicon ultra-0.5 10k filter tube was used again to filter out any molecules lower than 10 kDa molecular weights. This filtered solution was diluted to 500 µL by 10 mM EDTA in 0.1 M PBS solution and centrifuged at 12000 rpm for 15 min at 8° C. The solution was then diluted again using 10 mM EDTA in 0.1 M PBS solution to 500 µL and centrifuged again at 12000 rpm for 15 min at 8° C. After this second centrifuge process, the obtained solution was a thiol-linked anti-AMACR. The bioconjugation process is shown in FIG. 7. Thiol-linked anti-PSA solution was prepared in similar manner.

AMACR Biosensor and PSA Biosensor Fabrication Based on Thiol-Linked Antibody

Using the anti-AMACR solution as an example, it reacted with gold electrode surface forming a strong Au—S bond linking the antibody onto the gold working electrode. Thiol-linked anti-AMACR was firstly diluted by 0.15M NaCl and 10 mM EDTA in 0.1 M PBS solution to a concentration of 1.25 µg/mL. The gold biosensor was prepared in a batch of ten and cleaned as described in a previous study. The diluted thiol-linked anti-AMACR solution was vortexed. 20 µL of the solution at concentration of 1.25 µg/mL was drop casted onto cleaned gold biosensor for incubation of 8 hours at 4° C. The preparation step of PSA biosensor is similar.

Results

Figure 8A:
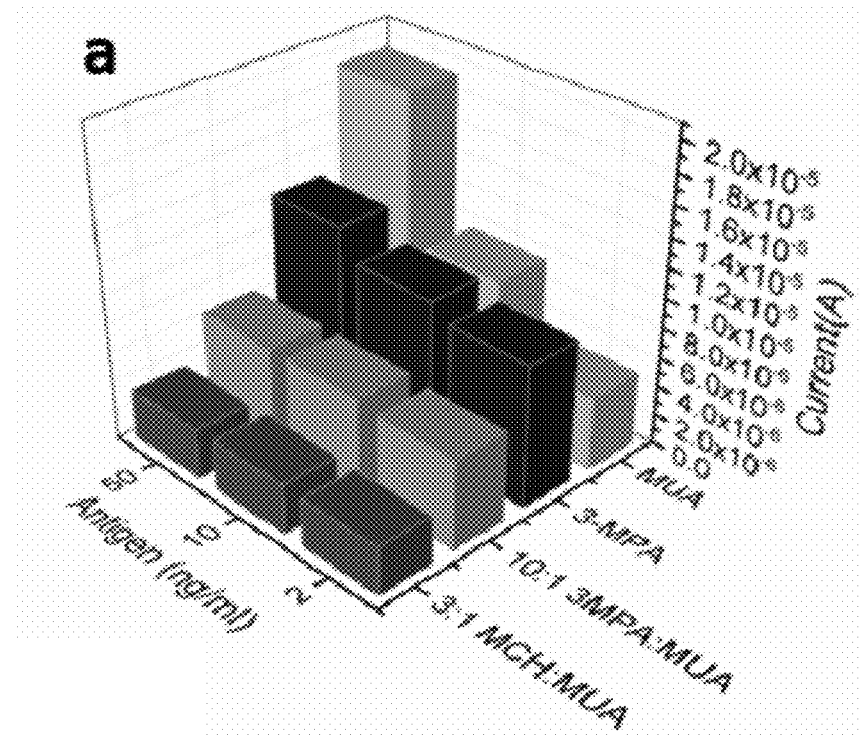
FIGS. 8(A-F) illustrates A) Sensitivity comparison on four different SAM system. B) EIS measurement on SAM1 and SAM1-antibody. C) EIS measurement on SAM3 and SAM3-antibody. D) EIS measurement on SAM5 and SAM5-antibody. E) EIS measurement on SAM6 and SAM6-antibody. F) EIS measurement on bare electrode and bio-conjugated-antibody layer.

Evaluation of the Effectiveness of Coverage and Antibody Bonding of Different SAM and Bioconjugated Systems The sensitivity and the reproducibility of the biosensors prepared using different SAM systems and bioconjugation mechanism were evaluated. Three different AMACR antigen concentrations (50 ng/mL, 10 ng/mL, 2 ng/mL) were prepared in 0.1M PBS and drop-casted onto the biosensors with different SAM systems incubating for 2 hours at room temperature. After the incubation, the biosensor was rinsed by 0.1M PBS solution and dried by nitrogen. Differential pulse voltammetry was used to measure the conductivity on the biosensor. 20 µL of a redox coupling solution, $K_4Fe(CN)_6$ and $K_3Fe(CN)_6$ of 5 mM each, was applied onto the biosensor surface. Of these six different SAM systems, SAM2 and SAM4 prepared biosensors showed unpromising reproducibility, and they were not be investigated any further. FIG. 8A shows the sensitivity comparison for the other four SAM monolayer systems studied as described in Table 2. SAM3 demonstrated the best sensitivity; and the difference among these four SAM modifications was minute and the sensitivity was at the level of $10^4$ to $10^5$ µA·µ $M^{-1}$-$cm^{-2}$ which was only fair. SAM1 system (3-MPA) retained the highest R-square value of these four SAM systems which was 0.698. This R-square value was significantly lower than that of the bioconjugation prepared biosensor, indicating a lower reproducibility of the SAM monolayer system for the detection of AMACR. The results of this study led us to apply bio-conjugation mechanism to prepare the biosensor for a better achievement of antibody-antigen recognition mechanism.

Figure 8B:
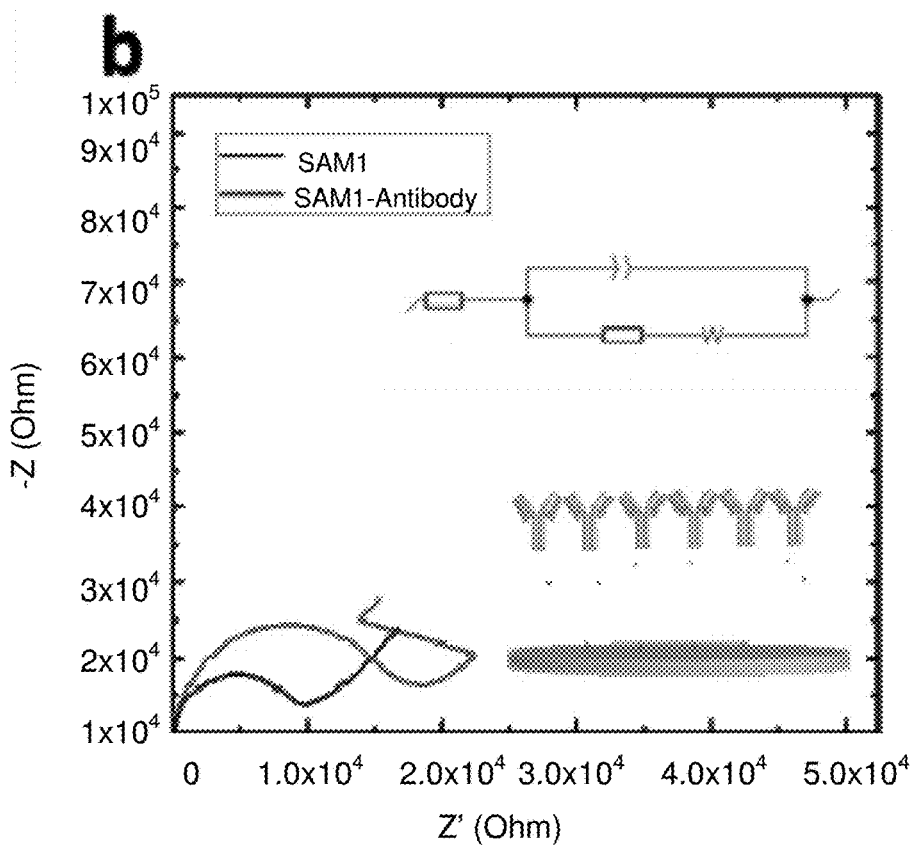
Figure 8C:
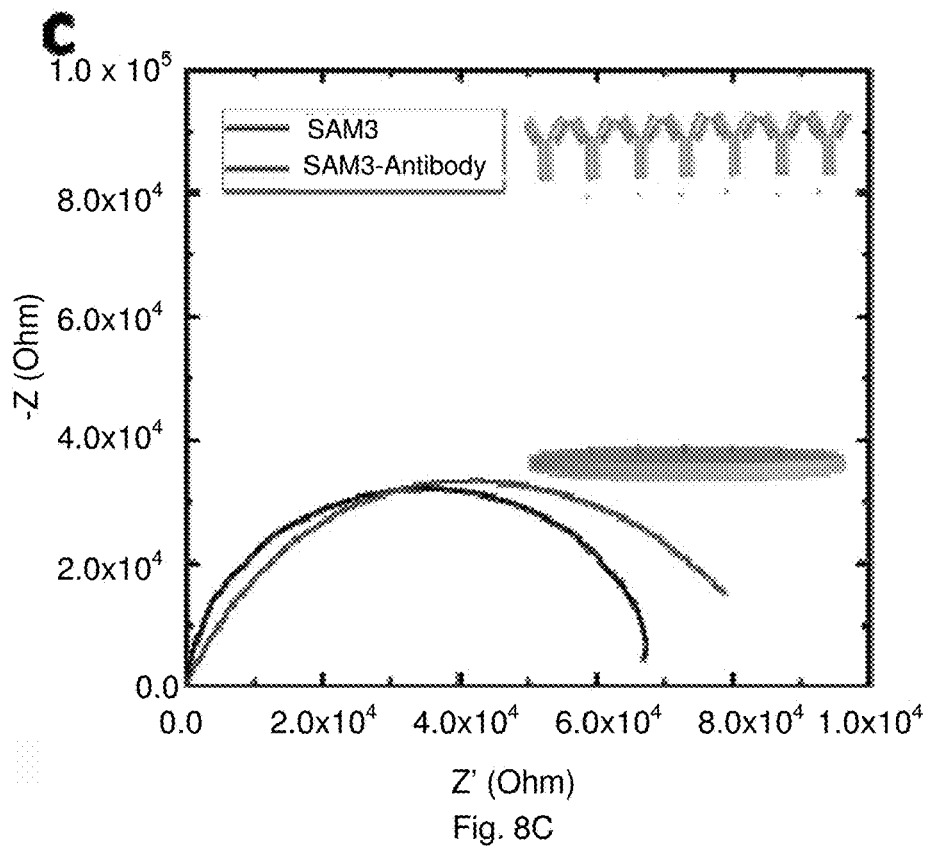
Figure 8D:
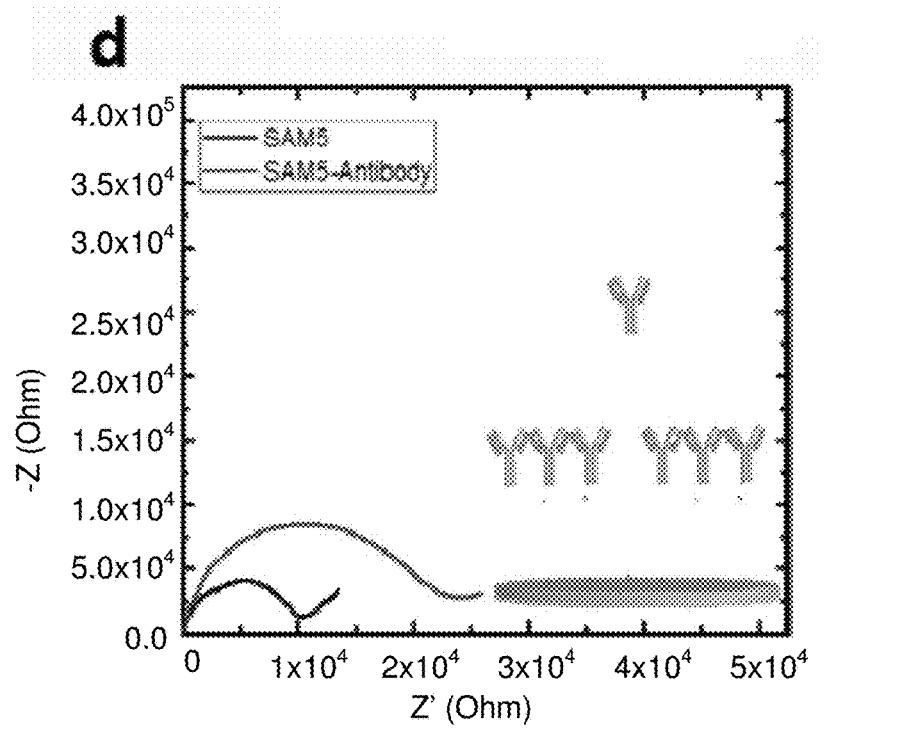
Figure 8E:
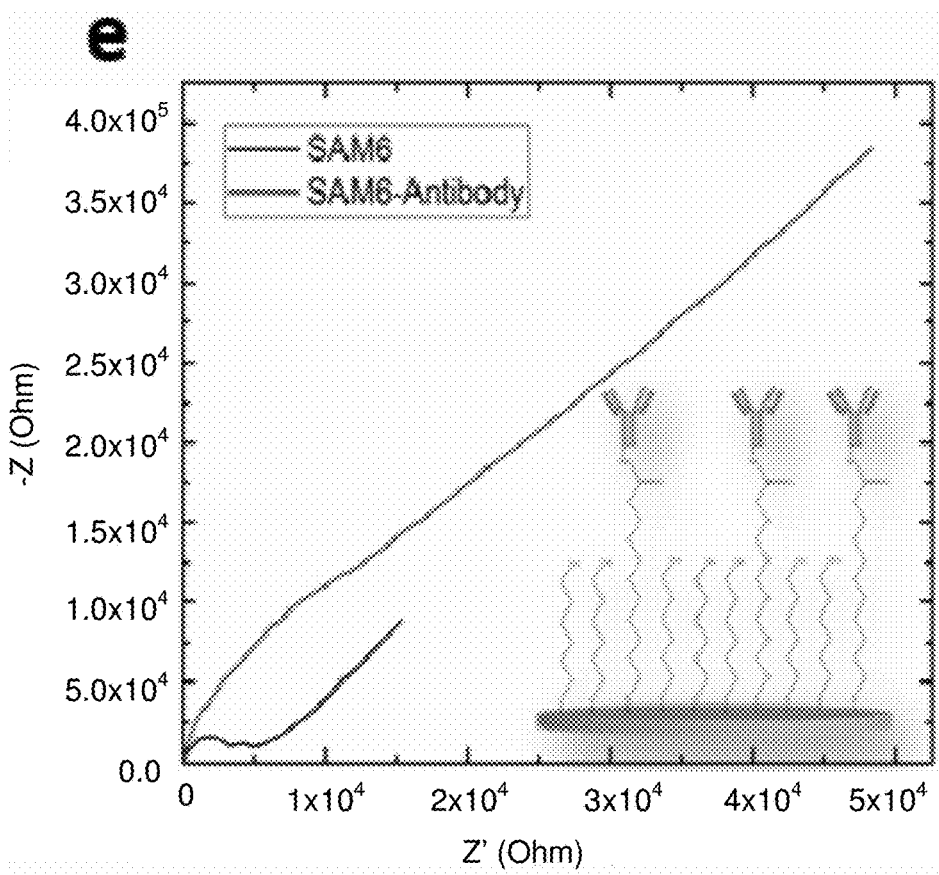
Figure 8F:
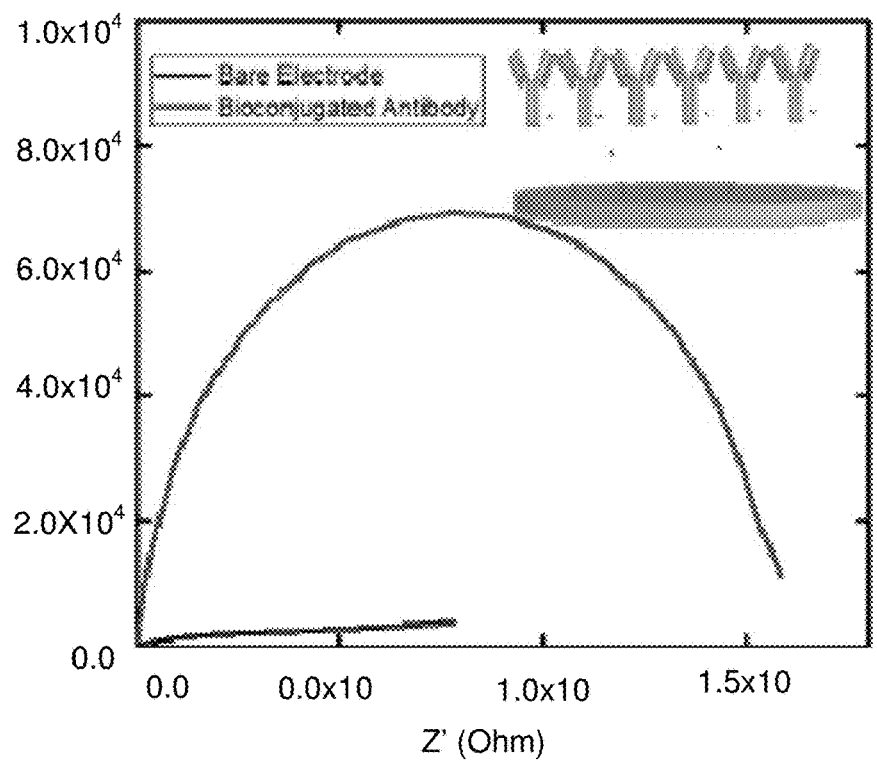

Electrochemical impedance spectroscopy (EIS) was used to assess the effectiveness of the antibody binding by different SAM techniques as well as the bioconjugation method. Using anti-AMACR protein as the example, four selected SAM systems and the bioconjugated modified biosensors were investigated. The impedance difference between SAM monolayer and antibody-bonded SAM monolayer as well as that between the bioconjugated biosensor and the antibody-bonded bioconjugated biosensor. A concentration of 1.25 µg/mL anti-AMACR protein was used for all the SAM and bioconjugated systems. The biosensors were incubated for 15 hours at 4° C. The biosensor was then rinsed by 0.1M PBS solution and dried by nitrogen gas. 20 μL of the redox coupling solution, $K_4Fe(CN)_6$ and $K_3Fe(CN)_6$ of 5 mM of each was applied on the surface for the electrochemical impedance spectroscopy (EIS) measurement. The AC frequency range for the EIS measurement was 0.01-10000 HZ. The Nyquist plots of this study are shown in FIGS. 3B, C, D, E, and F for four different SAM monolayers and FIG. 8G for the bioconjugation prepared antibody monolayer. The impedance difference before and after incubation of antibody was calculated by EC-Lab software fitting the Randle circuit as shown in FIG. 8B, in which R1 represented the solution resistance, R2 characterized the charge transfer resistance, W2 indicated the diffusion limited process and Q2 represented the electron transfer process. The difference of R2 value of each SAM system before/after incubation of antibody was used to display the impedance difference as shown in Table 3. The biggest impedance difference was shown from the bioconjugation method prepared biosensor in FIG. 8G with a calculated resistance value at 6635 Ohm, which was significantly larger than that of any SAM system, indicating the maximum efficiency of antibody coverage by using the bioconjugation for antibody monolayer formation.

TABLE 3

Resistance value difference modeled by Rnadle Circuit

| | Monolayer System | | | | |
|---|---|---|---|---|---|
| | SAM1 | SAM3 | SAM5 | SAM6 | Bioconjugation |
| Resistance Difference(Ohm) | 21.3 | 116 | 51.1 | 552.2 | 6635 |

Qualification of Bioconjugation Based Biosensor Surface using Atomic Force Microscopy (AFM)

Figure 9A:
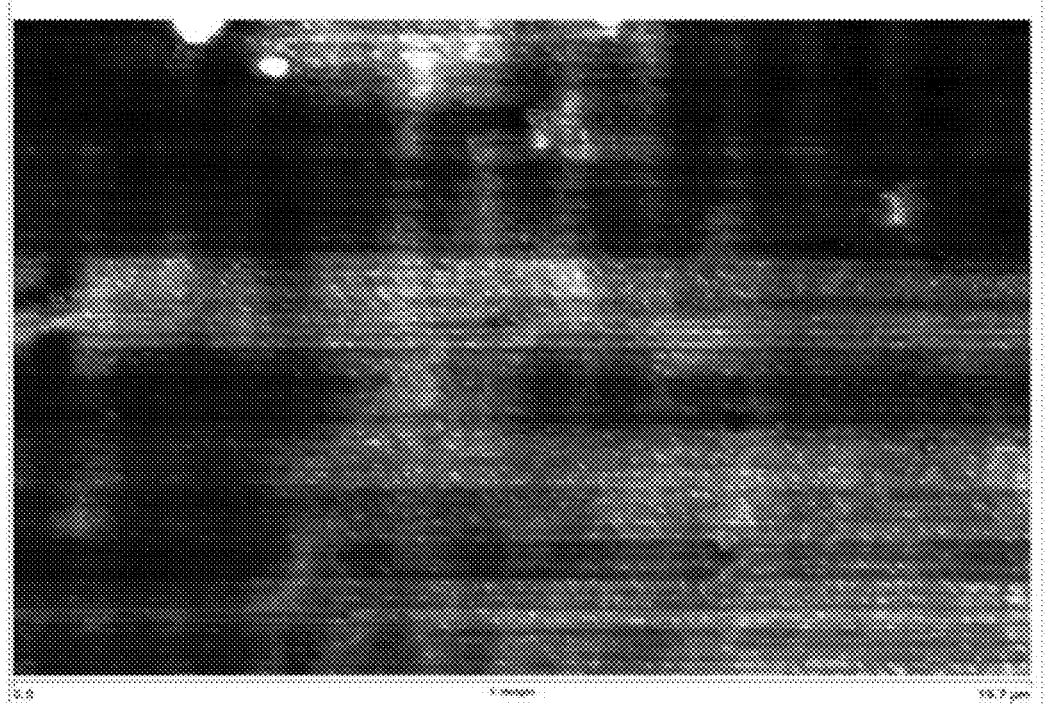
FIGS. 9(A-B) illustrate (A) A topography graph of bare gold electrode. (B) A topography graph of antibody film covered gold electrode.
Figure 9B:
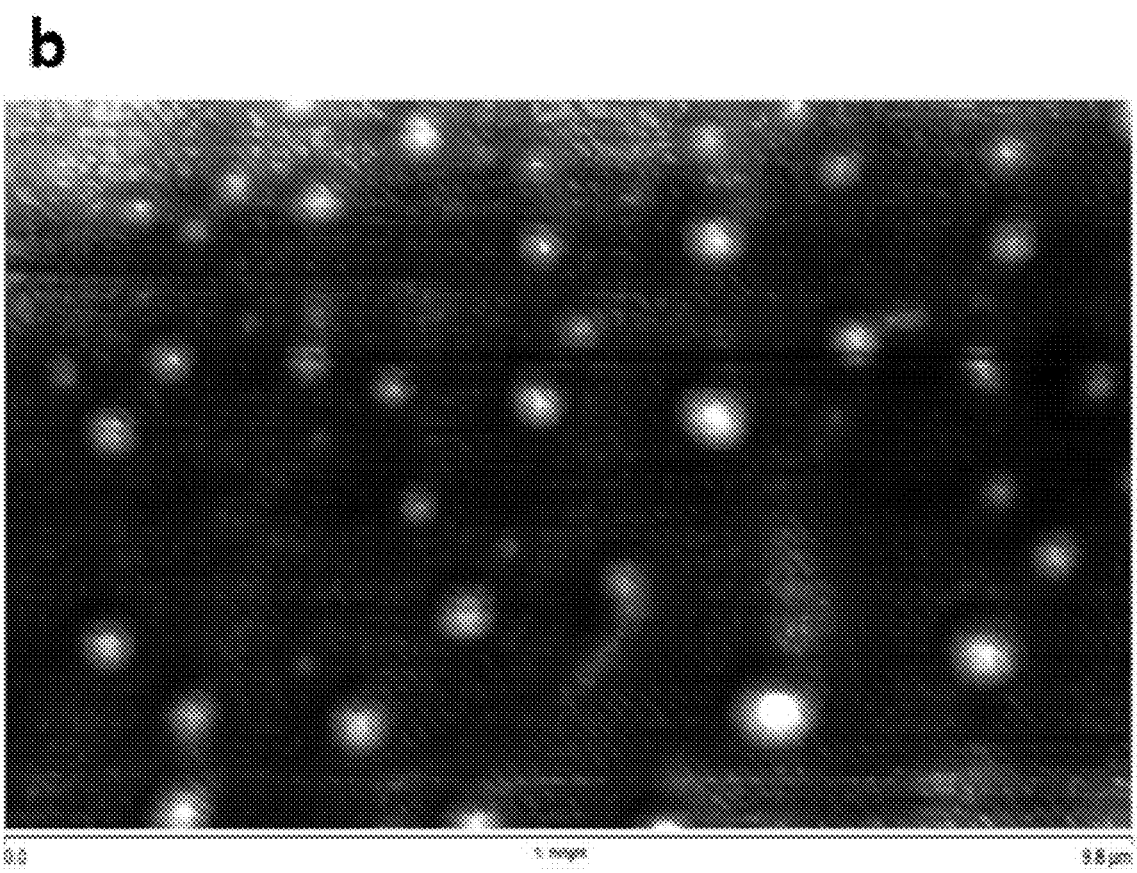

Atomic force microscopy was used to confirm the surface difference between bare gold working electrode and thiol-link AMACR antibody covered gold working electrode. A scan size of 20 μm×10 μm was applied at a scan rate of 0.513 Hz. FIGS. 9A and 9B show the topography of bare gold electrode image and thiol-linked antibody covered gold electrode image. FIG. 9A demonstrates a smooth gold electrode surface with a maximum height of 148 nm. FIG. 9B shows a more zigzag surface with a maximum height of 76000 nm. The white plumped ball shapes indicate a rougher topography with the existence of AMACR antibody. The white plumped balls also show very similar size with radius around 200-250 nm, indicating a homogeneous distribution of antibody on the surface. The qualification changes on the gold electrode surface observed by AFM is a solid proof of the capability of bioconjugation mechanism onbiosensor antibody film fabrication.

Figure 10A:
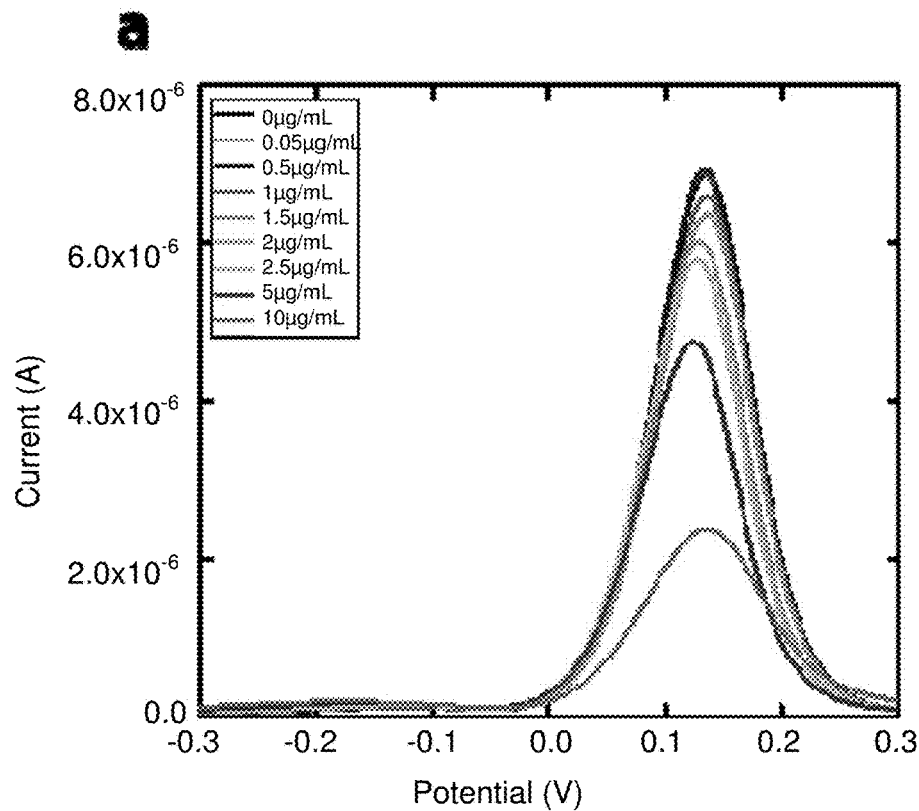
FIGS. 10(A-D) illustrate A) Differential pulse voltammetry measurements of AMACR antigen in 0.1M PBS. B) Differential pulse voltammetry measurements of AMACR antigen in undiluted human serum. C) Calibration curve based on the DPV measurement of AMACR antigen in 0.1 M PBS. D) Interference test on AMACR biosensor using PSA antigen.
Figure 10B:
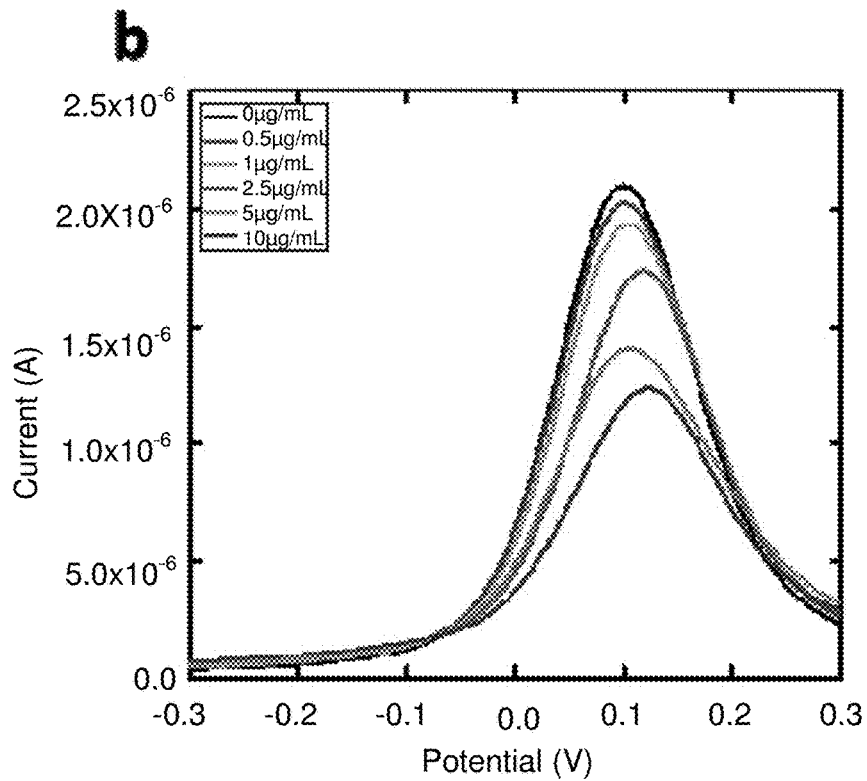
Figure 10C:
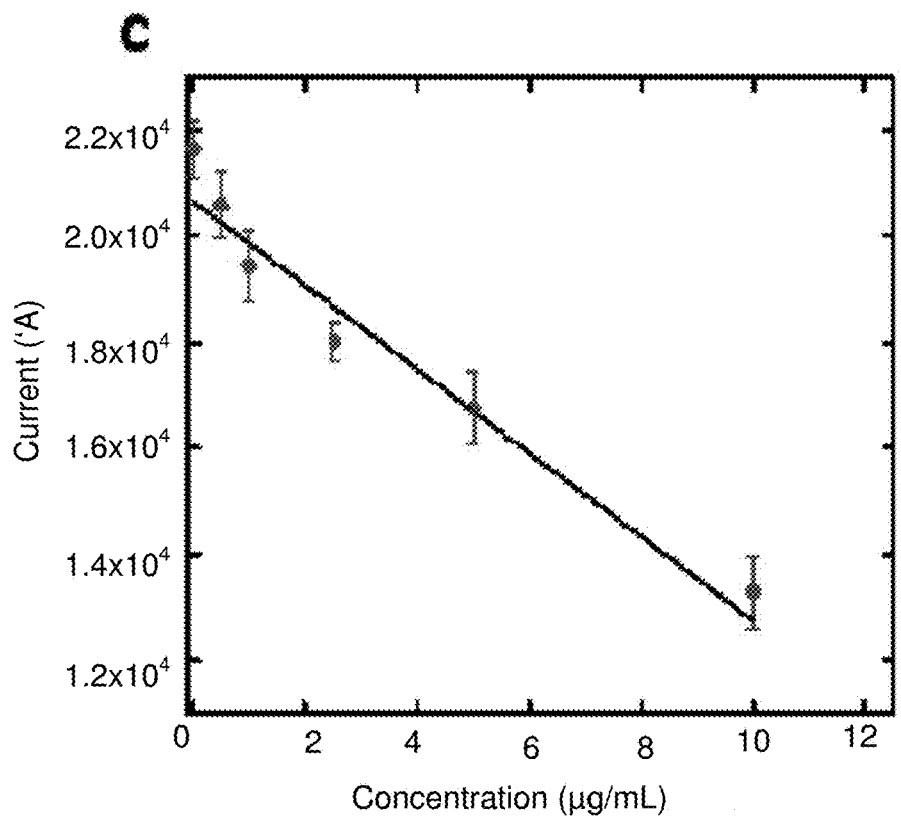

Differential Pulse Voltammetry Measurement of AMACR Antigen in PBS and Undiluted Human Serum The bioconjugation method prepared AMACR biosensor was then used for the detection of antigen of AMACR of different concentrations. Eight different concentrations of AMACR antigen were prepared in 0.1M PBS solution ranging from 10 μg/mL to 0.05 μg/mL. 20 μL of the antigen sample was placed onto the AMACR biosensor and was incubated for 1 hour atroom temperature. The AMACR biosensor was then rinsed by 0.1 M PBS and dried by nitrogen gas. 20 μL of a redox probe solution, of $K_4Fe(CN)_6$ and $K_3Fe(CN)_6$ of 5 mM each, was applied onto biosensor surface and DPV measurement was then made. DPV was conducted at the potential range from −0.3V to 0.3V. FIG. 5A shows the DPV measurement of eight different concentrations with a limitation of testing found at 0.05 μg/mL. Same experiment was also conducted using AMACR antigen in undiluted human serum with a limitation of detection as shown in FIG. 10B and the calibration is shown in FIG. 10C with a linear fit of $Y=2.30\times10^{-5}\ X-6.39\times10^{-6}$ and R-square value of 0.900.

Figure 11A:
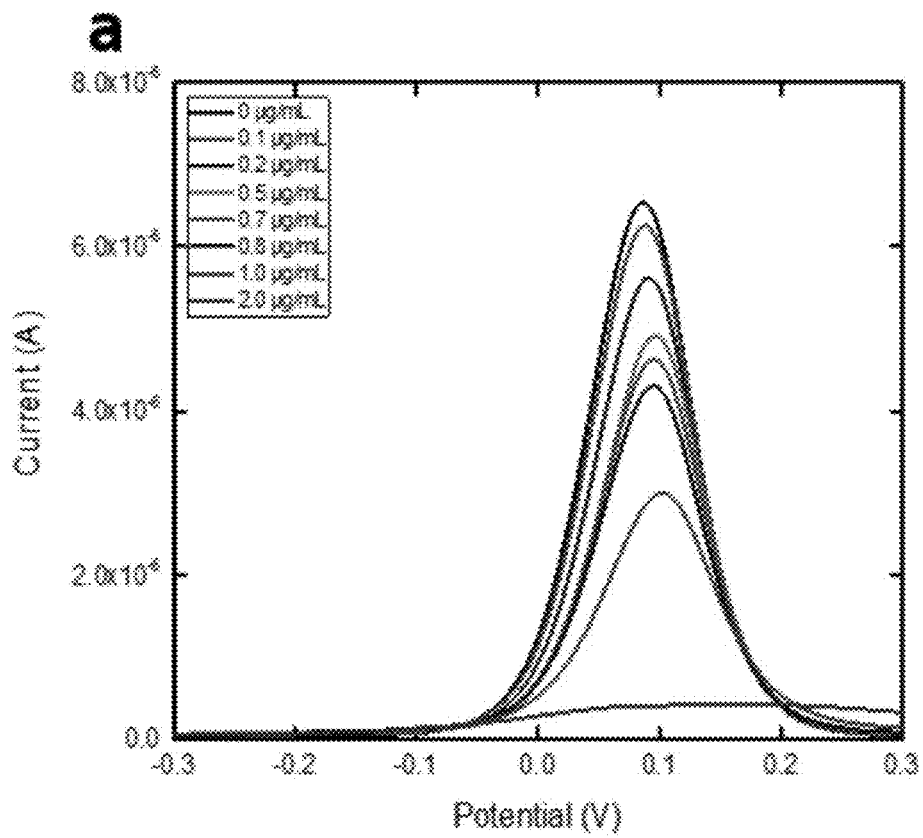
FIGS. 11(A-D) illustrate A) differential pulse voltammetry measurements of PSA antigen in 0.1M PBS. B) Differential pulse voltammetry measurements of PSA antigen in undiluted human serum. C) Calibration curve based on the DPV measurement of PSA antigen in undiluted human serum. D) Interference test on PSA biosensor using AMACR antigen.
Figure 11B:
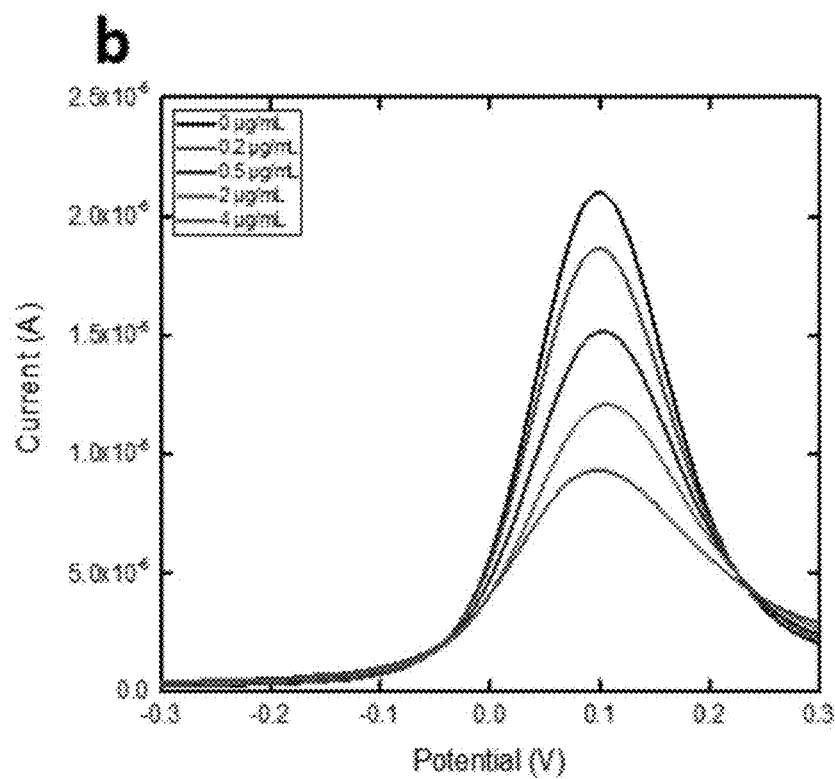
Figure 11C:
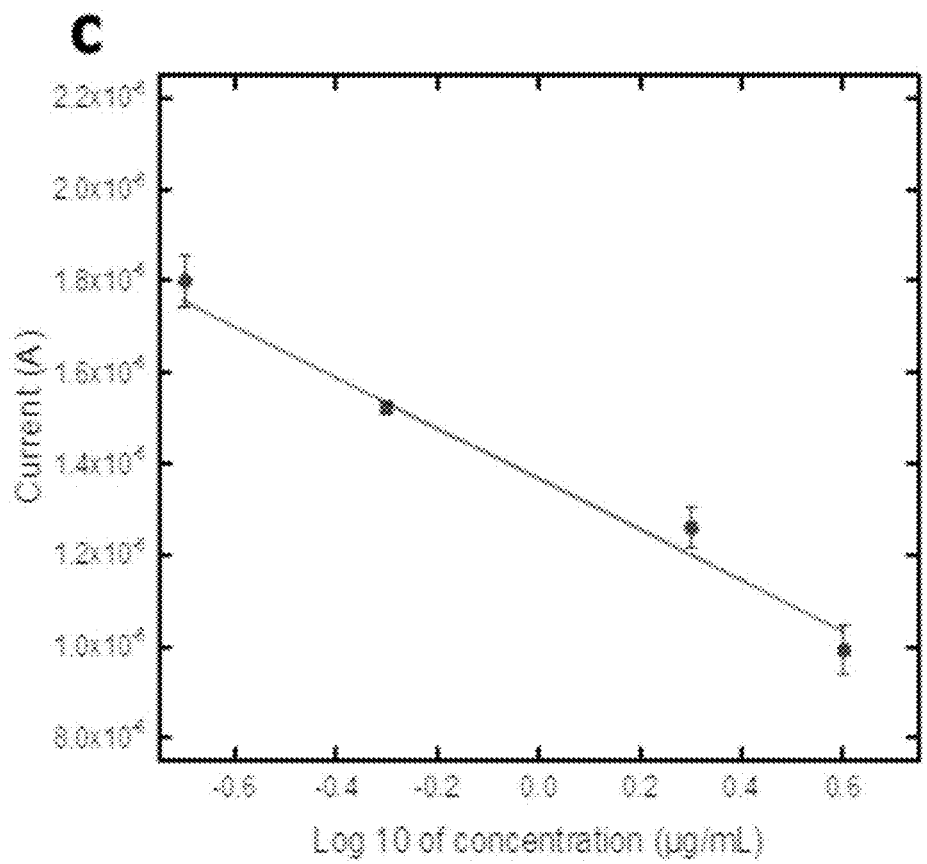

Differential Pulse Voltammetry Measurements of Prostate Specific Antigen (PSA) in PBS and Undiluted Human Serum For comprehensive detection of prostate cancer, prostate specific antigen (PSA) was also evaluated using bioconjugation mechanism prepared PSA biosensor and differential pulse voltammetry. PSA antigen in PBS solution was firstly tested based on an antibody concentration of 0.27 μg/mL. Concentrations of PSA antigen ranging from 2 μg/mL to 0.1 μg/mL were prepared in 0.1 M PBS solution. 20 μL of selected PSA antigen solution was drop-casted on the prepared PSA biosensor and incubated for 1 hr at room temperature. The PSA biosensor was then rinsed by 1 mL of 0.1M PBS solution and dried by nitrogen gas. 20 μL of a redox probe solution, of $K_4Fe(CN)_6$ and $K_3Fe(CN)_6$ of 5 mM each, was applied onto biosensor surface and DPV measurement was then made. DPV measurement was shown in FIG. 11A with a detection limit of 0.1 μg/mL. DPV measurement on PSA in undiluted human serum was also conducted with a PSA antigen concentration range of 0 to 4 μg/mL using an antibody concentration of 0.55 μg/mL. Same procedure as described in PBS test was applied for undiluted human test. DPV measurement was shown in FIG. 11B with a detection limit of 0.2 μg/mL and its calibration curve was shown in FIG. 11C with a linear fit of $Y=2.41\times10^{-5}\ X-4.33\times10^{-7}$ and R-square value of 0.967.

Interference Study of AMACR Biosensor and PSA Biosensor

Figure 10D:
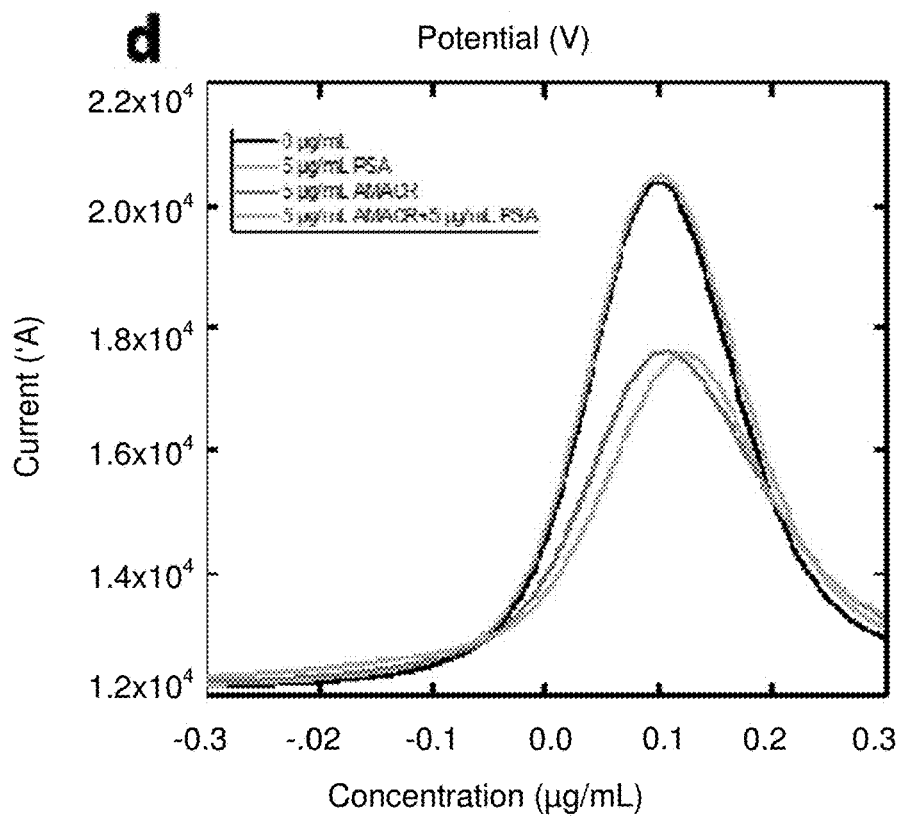
Figure 11D:
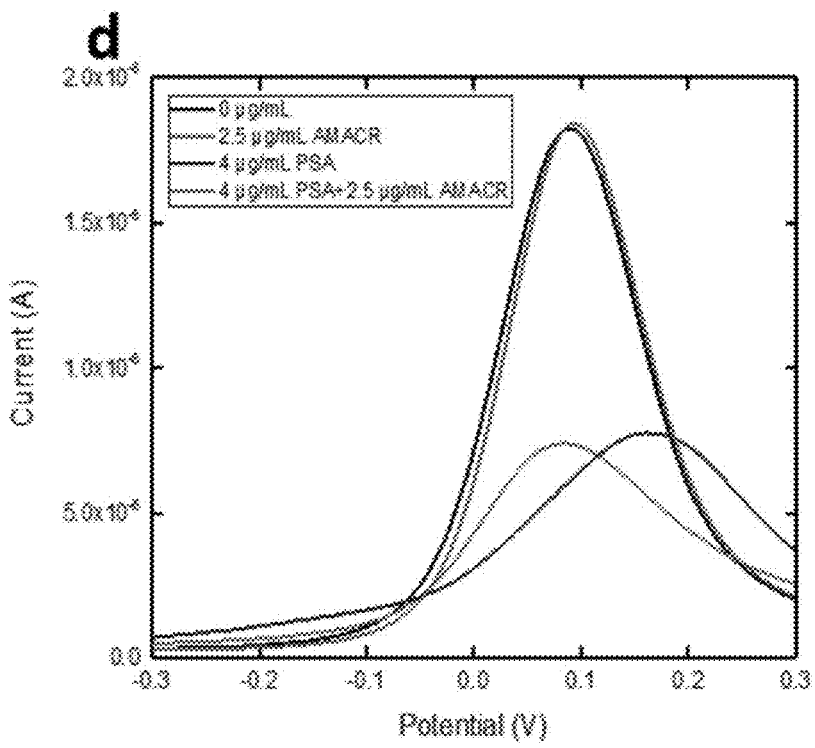

Interference studies on AMACR biosensor and PSA biosensor were conducted to confirm the selectivity of each biosensor. For AMACR biosensor study, undiluted human serum with a PSA antigen concentration of 5 μg/mL was mixed with 5 μg/mL of AMACR antigen. Same incubation and detection procedure were conducted as described previously. The DPV measurement result was shown in FIG. 10D, in which the serum with mixed PSA/AMACR antigens showed no current output difference with only AMACR antigen in the serum, indicating that PSA antigen did not interfere with the AMACR measurement by the AMACR biosensor. Similarly, for PSA biosensor study, undiluted human serum with an AMACR antigen concentration of 2.5 μg/mL was mixed with 4 μg/mL PSA antigen solution. Same incubation and detection procedure were conducted as described previously. The DPV measurement result was shown in FIG. 11D, in which the mixed PSA/AMACR antigens showed no current output difference with only PSA antigen in the serum, indicating AMACR antigen did not interfere with the PSA measurementby the PSA biosensor.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:
1. A method of forming an electrochemical sensor for detection of an analyte of interest, the method comprising;

providing an antibody that is selective to the analyte of interest;

conjugating a linker to a lysine residue of the antibody, the linker including an acyl group and a sulfhydryl group;

providing a sensor that includes a substrate; a working electrode formed on a surface of the substrate; a counter electrode formed on the surface of the substrate; and a dielectric layer covering a portion of the working electrode and counter electrode and defining an aperture exposing portions of surfaces of the working electrode and counter electrode; and reacting the linker conjugated to the antibody with the surface of the exposed portion of the working electrode to link the antibody to the working electrode.

2. The method of claim 1, wherein linker includes an N-hydroxysuccinimide ester that reacts with an amine group of the lysine residue and a sulfhydryl group that reacts with the surface of the working electrode.

3. The method of claim 2, wherein the linker includes at least one of N-succinimidyl S-acetylthioacetate or N-succinimidyl S-acetylthiopropionate.

4. The method of claim 1, wherein the sulfhydryl group of the linker is coupled to a protecting group the protecting group being removed prior to reaction of the sulfhydryl group with the surface of the exposed portion of the working electrode.

5. The method of claim 1, wherein the working electrode and the counter electrode comprise metalized films.

6. The method of claim 5, wherein the working electrode and counter electrode independently comprise gold, platinum, palladium, silver, alloys thereof, and composites thereof.

7. The method of claim 6, the metalized films are provided on the surface of the substrate by sputtering or coating the films on the surface and wherein the working electrode and the counter electrode are formed using laser ablation to define the dimensions of the working electrode and the counter electrode.

8. The method of claim 1, further comprising a reference electrode on the surface of the substrate, the dielectric covering a portion of the reference electrode.

9. The method of claim 1, the antibody comprising at least one of an anti-TDP-43, anti-AMACR, or anti-PSA antibody.

10. The method of claim 1, the antibody conjugated to the linker being linked to the surface of the working electrode by providing the antibody in a solution that is continuously flowed over the surface of the electrode.

11. The method of claim 1, wherein the surface of the working electrode is free of a self-assembled monolayer.

12. A method of forming an electrochemical sensor for detection of an analyte of interest, the method comprising;

providing an antibody that is selective to the analyte of interest;

reacting an N-hydroxysuccinimide ester linker that includes an acyl group and a sulfhydryl with a lysine residue of the antibody to conjugate the linker to the antibody;

providing a sensor that includes a substrate; a working electrode formed on a surface of the substrate; a counter electrode formed on the surface of the substrate; and a dielectric layer covering a portion of the working electrode and counter electrode and defining an aperture exposing portions of surfaces of the working electrode and counter electrode; and reacting the linker conjugated to antibody with the surface of the exposed portion of the working electrode to link the antibody to the working electrode.

13. The method of claim 12, wherein the N-hydroxysuccinimide ester linker includes at least one of N-succinimidyl S-acetylthioacetate or N-succinimidyl S-acetylthiopropionate.

14. The method of claim 12, wherein the working electrode and the counter electrode comprise metalized films selected from the group consisting gold, platinum, palladium, silver, alloys thereof, and composites thereof.

15. The method of claim 12, the antibody comprising at least one of an anti-TDP-43, anti-AMACR, or anti-PSA antibody.

16. The method of claim 12, the antibody conjugated to the linker being linked to the surface of the working electrode by providing the antibody in a solution that is continuously flowed over the surface of the electrode.

17. A sensor for the detection of an analyte in a biological sample comprising:

a substrate;

a working electrode formed on a surface of the substrate;

a counter electrode formed on the surface of the substrate;

a dielectric layer covering a portion of the working electrode and counter electrode and defining an aperture exposing other portions of the working electrode and counter electrode;

a measuring device for applying voltage potentials to the working electrode and counter electrode and measuring the current flow between the working electrode and counter electrode; and an antibody that is selective to the analyte of interest, the antibody being conjugated to a surface of the exposed portion of the working electrode with a linker, the linker comprising about 3 to about 6 atoms in length and including a first end and a second end, the first end including an acyl group that is bound to a lysine group of the antibody and the second end including a sulfhydryl group that is bound to the surface of the working electrode.

18. The sensor of claim 17, wherein the surface of the working electrode is free of a self-assembled monolayer.

19. The sensor of claim 17, the antibody comprising at least one of an anti-TDP-43, anti-AMACR, or anti-PSA antibody.

* * * * *